(12) United States Patent
Lamberth et al.

(10) Patent No.: US 7,189,873 B2
(45) Date of Patent: Mar. 13, 2007

(54) PROPARGYLETHER DERIVATIVES, A PROCESS FOR THEIR PREPARATION AND THEIR USE FOR CONTROLLING PHYTOPATHOGENIC MICROORGANISMS

(75) Inventors: Clemens Lamberth, Basel (CH); Martin Zeller, Muenchwilen (CH)

(73) Assignee: Syngenta Corp Protection, Inc., Greensboro, NC (US)

( * ) Notice: Subject to any disclaimer, the term of this patent is extended or adjusted under 35 U.S.C. 154(b) by 108 days.

(21) Appl. No.: 10/528,668

(22) PCT Filed: Oct. 9, 2003

(86) PCT No.: PCT/EP03/11218

§ 371 (c)(1),
(2), (4) Date: Mar. 22, 2005

(87) PCT Pub. No.: WO2004/033413

PCT Pub. Date: Apr. 22, 2004

(65) Prior Publication Data
US 2006/0167316 A1   Jul. 27, 2006

(30) Foreign Application Priority Data
Oct. 10, 2002   (GB)   .................................. 0223665.1

(51) Int. Cl.
C07C 233/05 (2006.01)
C07C 311/03 (2006.01)
A01N 37/18 (2006.01)
A01N 41/06 (2006.01)

(52) U.S. Cl. .................. 564/170; 564/88; 564/138; 564/139; 564/149; 564/150; 514/604; 514/614; 514/617

(58) Field of Classification Search ................ 564/88, 564/149, 150, 170, 138, 139; 514/604, 614, 514/617
See application file for complete search history.

(56) References Cited

U.S. PATENT DOCUMENTS 3,236,889 A    2/1966  Pawloski
6,469,005 B1 * 10/2002  Zeller et al. ................ 514/248

FOREIGN PATENT DOCUMENTS

DE         4319887      12/1994
EP         0398072      11/1990
WO      WO 9530651     11/1995
WO      WO 9617840      6/1996

* cited by examiner

Primary Examiner—Shailendra Kumar
(74) Attorney, Agent, or Firm—William A. Teoli, Jr.

(57) ABSTRACT

The invention relates to 4-propargyloxy-benzyl dervatives of the general formula (I) including the optical isomers thereof and mixtures of such isomers, wherein $R_1$ is hydrogen, optionally substituted alkyl, optionally substituted cycloalkyl or optionally substituted aryl; $R_2$, $R_3$, $R_5$, $R_6$, and $R_7$ are each independently of each other hydrogen or optionally substituted alkyl; $R_4$ is optionally substituted alkyl; X is O or N—$R_7$; and $R_8$ is a group $R_9$ is optionally substituted aryl or optionally substituted heteroaryl; $R_{10}$ and $R_{11}$ are each independently hydrogen, optionally substituted alkyl, optionally substituted alkenyl or optionally substituted alkynyl; $R_{12}$ is optionally substituted alkyl, optionally substituted cycloalkyl, optionally substituted aryl or optionally substituted heteroaryl; $R_{13}$ is hydrogen or optionally substituted alkyl, alkenyl or alkynyl; and $R_{14}$ is optionally substituted alkyl or optionally substituted amino. These compounds possess useful plant protecting properties and may advantageously be employed in agricultural practice for controlling or preventing the infestation of plants by phytopathogenic microorganisms, especially fungi

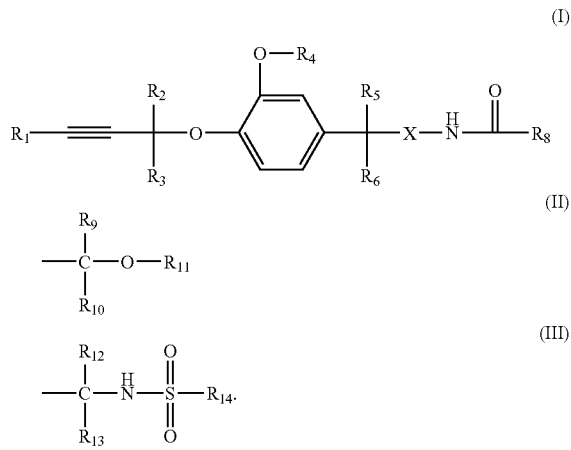

13 Claims, No Drawings

PROPARGYLETHER DERIVATIVES, A PROCESS FOR THEIR PREPARATION AND THEIR USE FOR CONTROLLING PHYTOPATHOGENIC MICROORGANISMS

This application is a 371 of International Application No. PCT/EP03/011218 filed Oct. 9, 2003, which claims priority to GB 0223665.1 filed Oct. 10, 2002, the contents of which are incorporated herein by reference.

The present invention relates to novel propargylether derivatives of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

Certain amino acid carbamates, mandelic acid derivatives and alkoximino acid derivatives have been proposed for controlling plant-destructive fungi, (for example, in EP-A-398072, WO 94/29267 and WO 96/17840). The action of those preparations is not, however, satisfactory in all aspects of agricultural needs. Surprisingly, with the compound structure of formula I, new kinds of microbicides having a high level of activity have been found.

The invention relates to propargylether derivatives of the general formula I

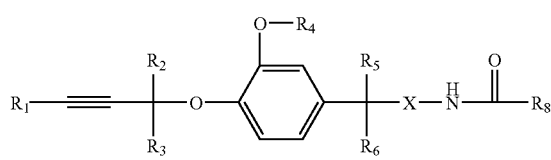

including the optical isomers thereof and mixtures of such isomers, wherein $R_1$ is hydrogen, optionally substituted alkyl, optionally substituted cycloalkyl or optionally substituted aryl;

$R_2$, $R_3$, $R_5$, $R_6$, and $R_7$ are each independently of each other hydrogen or optionally substituted alkyl;

$R_4$ is optionally substituted alkyl;

X is O or N—$R_7$; and $R_8$ is a group

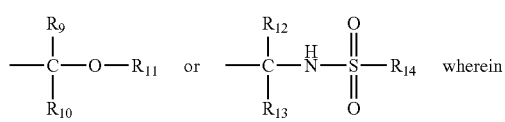

$R_9$ is optionally substituted aryl or optionally substituted heteroaryl;

$R_{10}$ and $R_{11}$, are each independently hydrogen, optionally substituted alkyl, optionally substituted alkenyl or optionally substituted alkynyl;

$R_{12}$ is optionally substituted alkyl, optionally substituted cycloalkyl, optionally substituted aryl or optionally substituted heteroaryl;

$R_{13}$ is hydrogen or optionally substituted alkyl, alkenyl or alkynyl; and $R_{14}$ is optionally substituted alkyl or optionally substituted amino.

In the above definition aryl includes aromatic hydrocarbon rings like phenyl, naphthyl, anthracenyl, phenanthrenyl, with phenyl being preferred.

Heteroaryl stands for aromatic ring systems comprising mono-, bi- or tricyclic systems wherein at least one oxygen, nitrogen or sulfur atom is present as a ring member. Typically heteroaryl comprises 1 to 4 identical or different heteroatoms selected from nitrogen, oxygen and sulfur, wherein the number of oxygen and sulfuratoms normally does not exceed one. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenyl-alkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; alkynyloxycarbonyl.

Optionally substituted alkyl, alkenyl, alkynyl or cycloalkyl groups may carry one or more substituents selected from halogen, alkyl, alkoxy, alkylthio, nitro, cyano, hydroxy, mercapto, alkylcarbonyl or alkoxycarbonyl. Preferably, the number of substituents is no more than three with the exception of halogen, where the alkyl groups may be perhalogenated. In the above definitions "halogen" or the prefix "halo" includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclo-butyl, cyclopentyl, cyclohexyl, cycloheptyl or cyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl (—$CH_2$—C≡CH), prop-2-ynyl (—C(—$CH_3$)≡CH), butyn-1-yl (—$CH_2$—$CH_2$—C≡CH), butyn-2-yl (—$CH_2$≡C—C—$CH_3$), 1-methyl-2-butynyl (—CH($CH_3$)—C≡C—$CH_3$), hexyn-1-yl(-[$CH_2$]$_4$—C≡CH), 1-ethyl-2-butynyl (—CH($CH_2$—$CH_3$)—C≡C—$CH_3$), or octyn-1-yl.

A haloalkyl group may contain one or more (identical or different) halogen atoms, and for example may stand for $CH_2Cl$, $CHCl_2$, $CCl_3$, $CH_2F$, $CHF_2$, $CF_3$, $CH_2CH_2Br$, $C_2Cl_5$, $C_2F_5$, $CH_2Br$, $CHClBr$, $CF_3CH_2$, etc.

The presence of at least one asymmetric carbon atom in the compounds of formula I means that the compounds may occur in optically isomeric and enantiomeric forms. As a result of the presence of a possible aliphatic C═C double bond, geometric isomerism may also occur. Formula I is intended to include all those possible isomeric forms and mixtures thereof.

Preferred subgroups of compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; or alkynyloxycarbonyl; or $R_1$ is hydrogen, $C_1$–$C_8$-alkyl, $C_3$–$C_8$-cycloalkyl, phenyl or naphthyl; phenyl and naphthyl being optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano and nitro; or $R_1$ is hydrogen, $C_1$–$C_6$-alkyl or $C_3$–$C_6$-cycloalkyl; or $R_2$ and $R_3$ are hydrogen or $C_1$–$C_6$-alkyl; or $R_2$ and $R_3$ are hydrogen; or $R_4$ is $C_1$–$C_6$-alkyl; or $R_5$ and $R_6$ are hydrogen or $C_1$–$C_6$-alkyl; or $R_5$ and $R_6$ are hydrogen X is oxygen or nitrogen; nitrogen being optionally substituted by hydrogen or $C_1$–$C_8$-alkyl; or $R_8$ is $C(R_9R_{10})$-$OR_{11}$ $R_9$ is aryl or heteroaryl, each optionally substituted by substituents selected from the group comprising alkyl, alkenyl, alkynyl, cycloalkyl, cycloalkyl-alkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl; or $R_9$ is phenyl, naphthyl, 1,3-biphenyl or 1,4-biphenyl, each optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_2$–$C_8$-haloalkylthio, $C_1$–$C_8$-alkylsulfonyl, halogen, cyano, nitro and $C_1$–$C_8$-alkoxycarbonyl; or $R_9$ is phenyl, naphthyl, 1,3-biphenyl or 1,4-biphenyl, each optionally substituted by one to three substituents selected from the group comprising $C_0$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, cyano, nitro and $C_1$–$C_6$-alkoxycarbonyl; or $R_{10}$ is hydrogen, $C_1$–$C_8$-alkyl, $C_1$–$C_8$-haloalkyl, $C_3$–$C_8$-alkenyl or $C_3$–$C_8$-alkynyl; or $R_{10}$ is hydrogen or $C_1$–$C_6$-alkyl; or $R_{10}$ is hydrogen; or $R_{11}$ is hydrogen, $C_1$–$C_8$-alkyl, $C_1$–$C_8$-haloalkyl, $C_3$–$C_8$-alkenyl or $C_3$–$C_8$-alkynyl; or $R_{11}$ is hydrogen, $C_1$–$C_8$-alkyl, $C_3$–$C_8$-alkenyl or $C_3$–$C_8$-alkynyl; or $R_{11}$ is hydrogen, $C_1$–$C_6$-alkyl or $C_3$–$C_6$-alkynyl; or $R_{12}$ is $C_1$–$C_8$-alkyl, $C_3$–$C_8$-cycloalkyl, phenyl or naphthyl; phenyl and naphthyl being optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, aryl, halogen, cyano and nitro; or $R_{12}$ is $C_1$–$C_6$-alkyl or $C_3$–$C_6$-cycloalkyl; or $R_{13}$ is hydrogen, $C_1$–$C_8$-alkyl, $C_1$–$C_8$-haloalkyl, $C_3$–$C_8$-alkenyl or $C_3$–$C_8$-alkynyl; or $R_{13}$ is hydrogen or $C_1$–$C_6$-alkyl; or $R_{13}$ is hydrogen; or $R_{14}$ is $C_1$–$C_8$-alkyl, $C_1$–$C_8$-haloalkyl, $C_1$–$C_8$-alkylamino or $C_1$–$C_8$-dialkylamino; or $R_{14}$ is $C_1$–$C_6$-alkyl or $C_1$–$C_6$-dialkylamino.

One preferred subgroup of the compounds of formula I consists of those compounds wherein $R_{10}$ is hydrogen or alkyl, X is oxygen, and $R_8$ is —$C(R_9R_{10})$—$OR_{11}$ and $R_{11}$ is hydrogen or alkynyl; or wherein X is oxygen, $R_8$ is —$C(R_{12}R_{13})NH$—$SO_2$—$R_{14}$, and $R_{12}$ is alkyl or branched alkyl.

Further preferred subgroups of the compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy; alkenyloxy; alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; or alkynyloxycarbonyl; and $R_4$ is alkyl; and $R_8$ is a group —$C(R_9R_{10})$—$OR_{11}$, $R_9$ is aryl or heteroaryl, each optionally substituted by substituents selected from to group comprising alkyl, alkenyl, alkynyl, cycloalkyl, cycloalkyl-alkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl; and $R_1$, is hydrogen; alkyl or alkynyl; or $R_8$ is a group —$C(R_{12}R_{13})NH$—$SO_2$—$R_{14}$, $R_{14}$ is alkyl or alkylamino; or wherein $R_1$ is hydrogen, $C_1$–$C_8$-alkyl, $C_3$–$C_8$-cycloalkyl; and $R_2$, $R_3$, $R_5$ and $R_6$ are hydrogen; and $R_4$ is $C_1$–$C_6$-alkyl; and $R_9$ is phenyl, naphthyl, 1,3-biphenyl or 1,4-biphenyl, each optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; and $R_{10}$ is hydrogen or $C_1$–$C_4$-alkyl; and $R_{11}$ is hydrogen, $C_1$–$C_8$-alkyl or $C_2$–$C_8$-alkynyl; and $R_{12}$ is $C_1$–$C_8$-alkyl, $C_3$–$C_6$-cycloalkyl, $C_3$–$C_8$-alkenyl, $C_3$–$C_8$-alkynyl; phenyl or benzyl wherein the phenyl and benzyl is optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; and $R_{13}$ is hydrogen or $C_1$–$C_4$-alkyl; and $R_{14}$ is $C_1$–$C_6$-alkyl; $C_1$–$C_6$-monoalkylamino or $C_1$–$C_6$-dialkylamino; or wherein $R_1$ is hydrogen or $C_1$–$C_6$-alkyl, and $R_2$, $R_3$, $R_5$ and $R_6$ are hydrogen; and $R_4$ is methyl or ethyl; and $R_9$ is phenyl or naphthyl each optionally substituted by one to three substituents selected from the group comprising $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, cyano, nitro and $C_1$–$C_6$-alkoxycarbonyl; and $R_{10}$ and $R_{13}$ are each hydrogen; and $R_{11}$, is hydrogen or $C_2$–$C_6$-alkynyl; and $R_{12}$ is $C_2$–$C_6$-alkyl or $C_3$–$C_6$-cycloalkyl; and $R_{14}$ is $C_1$–$C_6$-alkyl or $C_1$–$C_6$-dialkylamino.

Preferred individual compounds are:

2-hydroxy-N-(3-methoxy-4-prop-2-ynyloxy-benzyloxy)-2-phenyl-acetamide,

N-(3-methoxy-4-prop-2-ynyloxy-benzyloxy)-2-phenyl-2-prop-2-ynyloxy-acetamide, 2-hydroxy-N-(3-methoxy-4-pent-2-ynyloxy-benzyloxy)-2-phenyl-acetamide, N-(3-methoxy-4-pent-2-ynyloxy-benzyloxy)-2-phenyl-2-prop-2-ynyloxy-acetamide, 2-(4-chloro-phenyl)-2-hydroxy-N-(3-methoxy-4-prop-2-ynyloxy-benzyloxy)-acetamide, 2-(4-chloro-phenyl)-N-(3-methoxy-4-prop-2-ynyloxy-benzyloxy)-2-prop-2-ynyloxy-acetamide, 2-(4-chloro-phenyl)-2-hydroxy-N-(3-methoxy-4-pent-2-ynyloxy-benzyloxy)-acetamide, 2-(4-chloro-phenyl)-N-(3-methoxy-4-pent-2-ynyloxy-benzyloxy)-2-prop-2-ynyloxy-acetamide, 2-(4-bromo-phenyl)-2-hydroxy-N-(3-methoxy-4-prop-2-ynyloxy-benzyloxy)-acetamide, 2-(4-bromo-phenyl)-N-(3-methoxy-4-prop-2-ynyloxy-benzyloxy)-2-prop-2-ynyloxy-acetamide, 2-(4-bromo-phenyl)-2-hydroxy-N-(3-methoxy-4-pent-2-ynyloxy-benzyloxy)-acetamide, 2-(4-bromo-phenyl)-N-(3-methoxy-4-pent-2-ynyloxy-benzyloxy)-2-prop-2-ynyloxy-acetamide, 2-(3,4-dichloro-phenyl)-2-hydroxy-N-(3-methoxy-4-prop-2-ynyloxy-benzyloxy)-acetamide, 2-(3,4-dichloro-phenyl)-N-(3-methoxy-4-prop-2-ynyloxy-benzyloxy)-2-prop-2-ynyloxy-acetamide, 2-(3,4-dichloro-phenyl)-2-hydroxy-N-(3-methoxy-4-pent-2-ynyloxy-benzyloxy)-acetamide, 2-(3,4-dichloro-phenyl)-N-(3-methoxy-4-pent-2-ynyloxy-benzyloxy)-2-prop-2-ynyloxy-acetamide, (S)-2-methylsulfonylamino-N-(3-methoxy-4-prop-2-ynyloxy-benzyloxy)-3-methyl-butyramide, (S)-2-methylsulfonylamino-N-(3-methoxy-4-pent-2-ynyloxy-benzyloxy)-3-methyl-butyramide, (S)-N-{4-[3-(4-chloro-phenyl)-prop-2-ynyloxy]-3-methoxy-benzyloxy}-2-methylsulfonylamino-3-methyl-butyramide, (S)-2-ethylsulfonylamino-N-(3-methoxy-4-prop-2-ynyloxy-benzyloxy)-3-methyl-butyramide, (S)-N-(4-[3-(4-chloro-phenyl)-prop-2-ynyloxy]-3-methoxy-benzyloxy)-2-N,N'-dimethylamino-sulfonylamino-3-methyl-butyramide, 2-(4-ethyl-phenyl)-2-hydroxy-N-(3-methoxy-4-prop-2-ynyloxy-benzyloxy)-acetamide, 2-(4-ethyl-phenyl)-2-hydroxy-N-(3-methoxy-4-pent-2-ynyloxy-benzyloxy)-acetamide, (S)-2-ethylsulfonylamino-N-(3-methoxy-4-pent-2-ynyloxy-benzyloxy)-3-methyl-butyramide, (S)-N-{4-[3-(4-chloro-phenyl)-prop-2-ynyloxy]-3-methoxy-benzyloxy}-2-ethanesulfonylamino-3-methyl-butyramide, hydroxy-phenyl-acetic acid N'-(3-methoxy-4-prop-2-ynyloxy-benzyl)-hydrazide, phenyl-prop-2-ynyloxy-acetic acid N'-(3-methoxy-4-prop-2-ynyloxy-benzyl)-hydrazide, hydroxy-phenyl-acetic acid N'-(3-methoxy-4-pent-2-ynyloxy-benzyl)-hydrazide, phenyl-prop-2-ynyloxy-acetic acid N'-(3-methoxy-4-pent-2-ynyloxy-benzyl)-hydrazide, (4-chloro-phenyl)-hydroxy-acetic acid N'-(3-methoxy-4-prop-2-ynyloxy-benzyl)-hydrazide, (4-chloro-phenyl)-prop-2-ynyloxy-acetic acid N'-(3-methoxy-4-prop-2-ynyloxy-benzyl)-hydrazide, (4-chloro-phenyl)-hydroxy-acetic acid N'-(3-methoxy-4-pent-2-ynyloxy-benzyl)-hydrazide, (4-chloro-phenyl)-prop-2-ynyloxy-acetic acid N'-(3-methoxy-4-pent-2-ynyloxy-benzyl)-hydrazide, (4-bromo-phenyl)-hydroxy-acetic acid N'-(3-methoxy-4-prop-2-ynyloxy-benzyl)-hydrazide, (4-bromo-phenyl)-prop-2-ynyloxy-acetic acid N'-(3-methoxy-4-prop-2-ynyloxy-benzyl)-hydrazide, (4-bromo-phenyl)-hydroxy-acetic acid N'-(3-methoxy-4-pent-2-ynyloxy-benzyl)-hydrazide, (4-bromo-phenyl)-prop-2-ynyloxy-acetic acid N'-(3-methoxy-4-pent-2-ynyloxy-benzyl)-hydrazide, (3,4-dichloro-phenyl)-hydroxy-acetic acid N'-(3-methoxy-4-prop-2-ynyloxy-benzyl)-hydrazide, (3,4-dichloro-phenyl)-prop-2-ynyloxy-acetic acid N'-(3-methoxy-4-prop-2-ynyloxy-benzyl)-hydrazide, (3,4-dichloro-phenyl)-hydroxy-acetic acid N'-(3-methoxy-4-pent-2-ynyloxy-benzyl)-hydrazide, (3,4-dichloro-phenyl)-prop-2-ynyloxy-acetic acid N'-(3-methoxy-4-pent-2-ynyloxy-benzyl)-hydrazide, N-{(S)-1-[N'-(3-methoxy-4-prop-2-ynyloxy-benzyl)-hydrazinocarbonyl]-2-methyl-propyl}-methylsulfonamide, N-{(S)-1-[N'-(3-methoxy-4-pent-2-ynyloxy-benzyl)-hydrazinocarbonyl]-2-methyl-propyl}-methylsulfonamide, N-[(S)-1-(N'-{4-[3-(4-chloro-phenyl)-prop-2-ynyloxy]-3-methoxy-benzyl}-hydrazinocarbonyl)-2-methyl-propyl]-methylsulfonamide, N-{(S)-1-[N'-(3-methoxy-4-prop-2-ynyloxy-benzyl)-hydrazinocarbonyl]-2-methyl-propyl}-ethylsulfonamide, N-{(S)-1-[N'-(3-methoxy-4-pent-2-ynyloxy-benzyl)-hydrazinocarbonyl]-2-methyl-propyl}-ethylsulfonamide, and N-[(S)-1-(N'-{4-[3-(4-chloro-phenyl)-prop-2-ynyloxy]-3-methoxy-benzyl}-hydrazinocarbonyl)-2-methyl-propyl]-ethylsulfonamide.

The propargylether derivatives of formula I may be obtained according to one of the processes of Schemes 1 to 3:

Scheme 1:

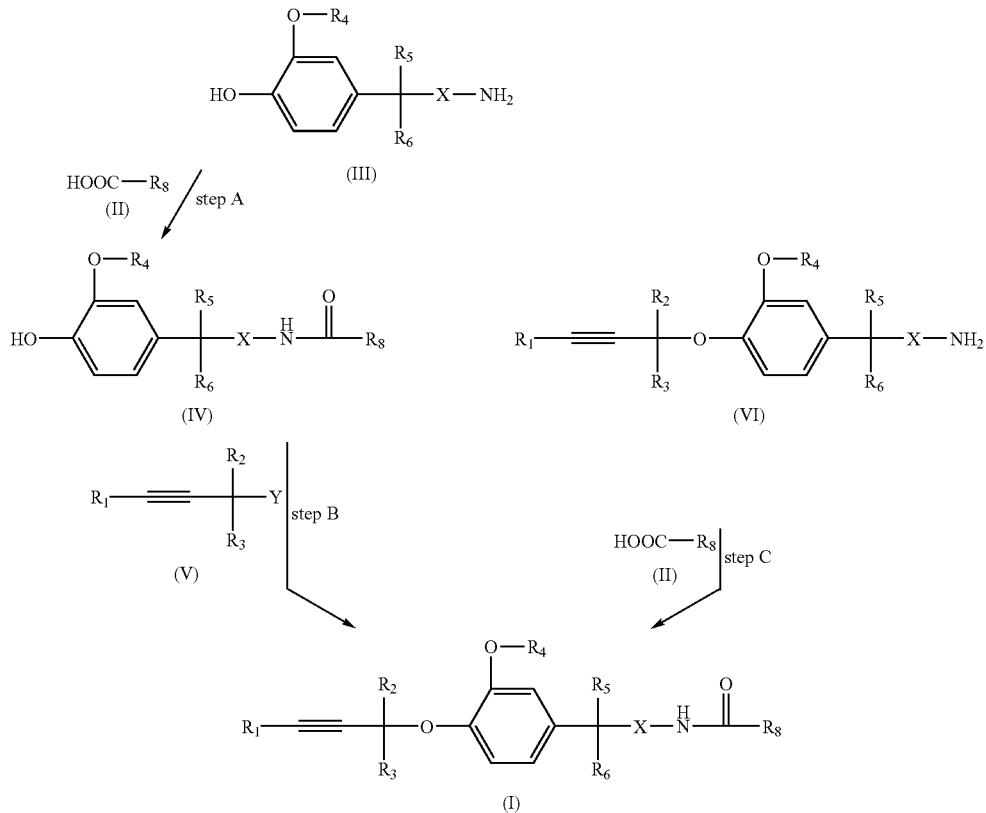

Step A: An acid of formula II or a carboxy-activated derivative of an acid of formula II wherein $R_8$ is as defined for formula I is reacted with an amino-derivative of formula III wherein $R_4$, $R_5$, $R_6$ and X are as defined for formula I, optionally in the presence of a base and optionally in the presence of an inert solvent.

Carboxy-activated derivatives of the acid of formula II for the purpose of this invention encompass all derivatives of compounds of formula II having an activated carboxyl group like an acid halide, such as an acid chloride, like symmetrical or mixed anhydrides, such as mixed anhydrides with O-alkylcarbonates, like activated esters, such as p-nitrophenylesters or N-hydroxysuccinimidesters, as well as in-situ-formed activated forms of the acid of formula II with condensating agents, such as dicyclohexylcarbodiimide, carbonyldiimidazole, benzotriazol-1-yloxy-tris(dimethylamino)phosphonium hexafluorophosphate, O-benzotriazol-1-yl N,N,N',N'-bis(pentamethylene)uronium hexafluorophosphate, O-benzotriazol-1-yl N,N,N',N'-bis(tetramethylene)uronium hexafluorophosphate, O-benzotriazol-1-yl N,N,N',N'-tetramethyluronium hexafluorophosphate or benzotriazol-1-yloxy-tripyrrolidinophosphonium hexafluorophosphate. The mixed anhydrides of the acids of the formula II may be prepared by reaction of an acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, N-methyl-piperidine or N-methyl-morpholine.

The present reaction is preferably performed in an inert solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitriles e.g. acetonitrile; or ethers e.g. diethylether, tert-butyl-methylether, dioxane or tetrahydrofurane or water. It is also possible to use mixtures of these solvents. The reaction is performed optionally in the presence of an organic or inorganic base like a tertiary amine, e.g. triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from −80° C. to +150° C., preferentially at temperatures ranging from −40° C. to +40° C.

Step B: The compounds of formula I may then finally be prepared by reaction of a phenol of formula IV wherein $R_4$, $R_5$, $R_6$, $R_8$ and X are as defined for formula I with a compound of formula V wherein $R_1$, $R_2$ and $R_3$ are as defined for formula I and wherein Y is a leaving group like a halide such as a chloride or bromide or a sulfonic ester such as a tosylate, mesylate or triflate.

The reaction is advantageously performed in an inert solvent like aromatic, non-aromatic or halogenated hydrocarbons, such as chlorohydrocarbons e.g. dichloromethane or toluene; ketones e.g. acetone or 2-butanone; esters e.g. ethyl acetate; ethers e.g. diethylether, tert-butyl-methylether, dioxane or tetrahydrofurane, amides e.g. dimethylformamide, nitrites e.g. acetonitrile, alcohols e.g. methanol, ethanol, isopropanol, n-butanol or tert-butanol, sulfoxides e.g. dimethylsulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80° C. to +200° C., preferentially at temperatures ranging from 0° C. to +120° C.

Step C: Alternatively to the sequence of steps A and B, an acid of formula II or a carboxy-activated derivative of an acid of formula II wherein $R_8$ is as defined for formula I may be reacted with an amino-derivative of formula VI wherein $R_1$, $R_2$, $R_3$, $R_4$, $R_5$, $R_6$ and X are as defined for formula I under the same conditions as defined for step A, optionally in the presence of a base and optionally in the presence of a diluting inert solvent.

Scheme 2:

Example for the preparation of intermediates of formula IV (wherein X is nitrogen and $R_6$ is hydrogen)

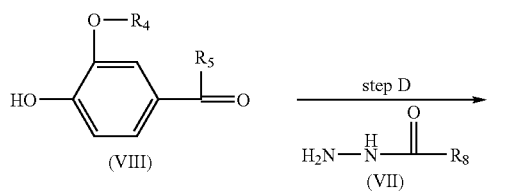

(VIII)

(VII)

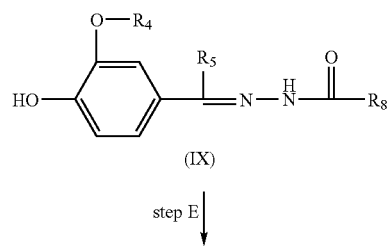

(IX)

step E

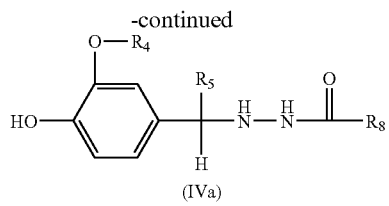

(IVa)

Step D: An acid hydrazide of formula VII wherein $R_8$ is as defined for formula I is reacted with a carbonyl compound of formula VIII wherein $R_4$ and $R_5$ are as defined for formula I. The reaction corresponds to a standard hydrazone formation and is with advantage performed in an inert solvent capable of forming azeotropic evaporates. The reaction may further be catalyzed by the presence of a mineral acid such as hydrochloric acid or sulfuric acid or an organic acid like formic acid or acetic acid. Water is eliminated during the condensation reaction, which preferably is continuously separated from the reaction mixture by azeotropic destillation, e.g. by using a Dean-Stark trap. Suitable solvents for this purpose include aromatic hydrocarbons like benzene, toluene and xylene or chlorinated hydrocarbons like methylene chloride or chloroform.

Step E: An acylhydrazone of formula IX wherein $R_4$, $R_5$ and $R_8$ are as defined for formula I is reduced to a compound of formula IVa wherein $R_4$, $R_5$ and $R_8$ are as defined for formula I by reaction with reducing agents like hydrogen or hydrazine In the presence of a suitable catalyst such as rhodium, platinum or palladium on carbon, or by reductive transformation with a metal hydride such as sodium borohydride, sodium cyanoborohydride or lithium aluminumhydride under conditions known per se (K. Shanker et al., *Arch. Pharm.* (Weinheim), 317, 890 (1984). The hydrogenation reaction is preferably performed in a solvent like esters e.g. ethyl acetate; amides e.g. N,N-dimethylformamide; or carboxylic acids, e.g. acetic acid; the transformations with metal hydride are preferably performed in a solvent like ethers e.g. diethylether, tert-butyl-methylether, dioxane or tetrahydrofurane; alcohols e.g. methanol or ethanol. It is also possible to use mixtures of these solvents. Furthermore the hydrogenation reaction can be performed at pressures between atmospheric pressure and 120 bar, preferentially at pressures ranging from 1 to 80 bar.

Scheme 3:

Example for the preparation of intermediates of formula VI (X=O)

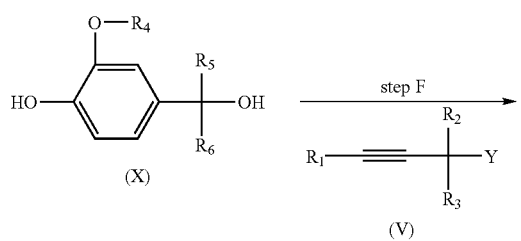

(X)

(V)

step F

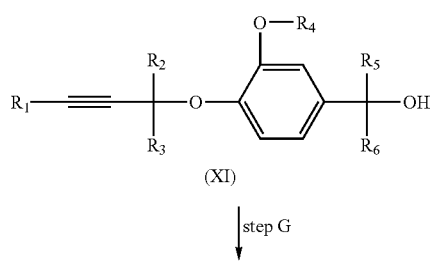

(XI)

step G

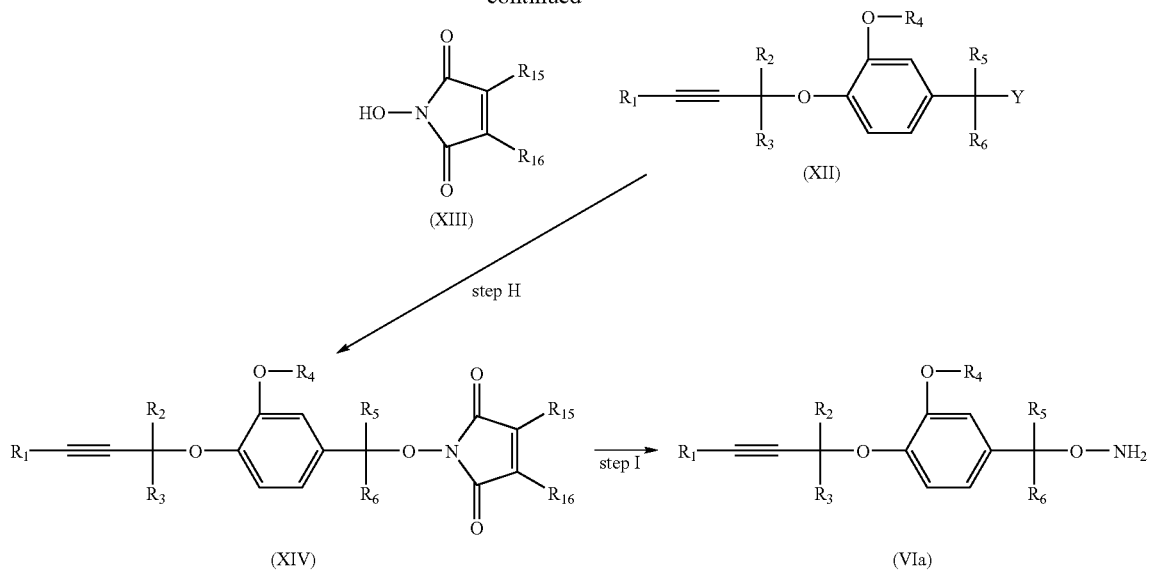

Step F: A phenol of formula X wherein $R_4$, $R_5$ and $R_6$ are as defined for formula I is reacted with a compound of formula V wherein $R_1$, $R_2$ and $R_3$ are as defined for formula I and wherein Y is a leaving group like a halide such as a chloride or bromide or a sulfonic ester such as a tosylate, mesylate or triflate under the same conditions as defined for step B in Scheme 1.

Step G: An alcohol of formula XI wherein $R_1$, $R_2$, $R_3$, $R_4$, $R_5$ and $R_6$ are as defined for formula I is transformed into a compound of formula XII wherein $R_1$, $R_2$, $R_3$, $R_4$, $R_5$ and $R_6$ are as defined for formula I and wherein Y is a leaving group like a halide such as a chloride or bromide or a sulfonic ester such as a tosylate, mesylate or triflate. The reaction can be achieved by converting the compound of formula XI e.g. with hydrochloric acid, hydrogen bromide, phosphorus tetrabromide or thionyl chloride as reagent to a halide; or with mesyl chloride or tosyl chloride as reagent to a sulfonic ester.

Step H: A compound of formula XII wherein $R_1$, $R_2$, $R_3$, $R_4$, $R_5$ and $R_6$ are as defined for formula I is reacted with a compound of formula XIII wherein $R_{15}$ and $R_{16}$ are hydrogen, halogen, methyl or part of an annelated benzene ring under conditions known per se for the formation of N-alkoxyimides (G. L. Verdine et al., *J. Am. Chem. Soc.*, 123, 398 (2001).

Step I: A compound of formula XIV wherein $R_1$, $R_2$, $R_3$, $R_4$, $R_5$ and $R_6$ are as defined for formula I and $R_{15}$ and $R_{16}$ are hydrogen, halogen, methyl or part of an annelated benzene ring is reacted with an amine derivative, like methylamine or butylamine or a hydrazine derivative, such as hydrazine, hydrazine hydrate or methylhydrazine under conditions known per se for the cleavage of N-alkoxyimides (M. P. Kirkup, *Tetrahedron Lett.*, 30, 6809 (1989).

The compounds of formula I are oils or solids at room temperature and generally stable when stored at ambient temperatures in a warehouse. These compounds are distinguished from known compounds of the chemical class by their valuable microbicidal properties. They can be used in the agricultural sector or related fields preventively and curatively in the control of phytopathogenic or plant-destructive microorganisms. The compounds of formula I according to the invention are distinguished at low rates of concentration not only by outstanding microbicidal, especially fungicidal activity but also by being especially well tolerated by plants.

Surprisingly, it has now been found that the compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. *Cercospora*), Basidiomycetes (e.g. *Puccinia*) and Ascomycetes (e.g. *Erysiphe* and *Venturia*) and especially against Oomycetes (e.g. *Plasmopara*, *Peronospora*, *Pythium* and *Phytophthora*). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I may be readily mixed with other fungicides in prefabricated compositions or as so-called tank-mixtures, exhibiting resulting in some cases unexpected resulting synergistic activities.

As ad-mixing components which are particularly suitable the azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, R-benalayxl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; HEC 5725 (proposed common name fluoxastrobin), orysastrobin (proposed common name), dithiocarbamates, such as ferbam, mancozeb, maneb, metiram, propineb, thiram, zineb, ziram; N-halomethylthiotetrahydro-phthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothalisopropyl; organo-P-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-L190 (proposed name: flumorph or flumorlin), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, DPX-KQ 926 (proposed comon name proquinazid), JAU 6476 (proposed common name prothioconazole), IKF-916 (cyazofamid), kasugamycin, methasulfocarb, metrafenone, boscalid (nicobifen), pencycuron, phthalide, polyoxins, probenazole, propamocarb, pyroquilon, quinoxyfen, quintozene, sulfur, triazoxide, tricyclazole, triforine, validamycin, zoxamide (RH7281).

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius.

PREPARATION EXAMPLES

Example A1.1

2-(4-Chloro-phenyl)-2-hydroxy-N-(3-methoxy-4-pent-2-ynyloxy-benzyloxy)-acetamide

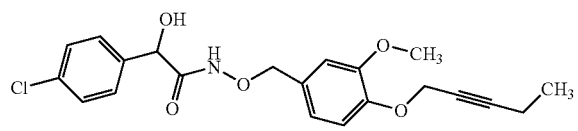

a) (3-Methoxy-4-pent-2-ynyloxy-phenyl)-methanol

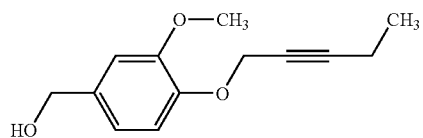

Sodium methoxide (36 ml of a 5.4 M solution in methanol, 0.20 mol) is added to a solution of 4-hydroxymethyl-2-methoxy-phenol (25 g, 0.16 mol) in 250 ml of methanol. Pentinyl chloride (18.5 g, 0.18 mol) is added and the mixture is heated to reflux for 4 hours. After evaporation of the solvent, the residue is taken up in ethyl acetate and washed with water and brine. The organic layer is dried over magnesium sulfate and evaporated. The residue is submitted to flash-chromatography on silica gel (ethyl acetate/hexane 1:2) to give (3-.methoxy-4-pent-2-ynyloxy-phenyl)-methanol as yellow oil.

$^1$H-NMR (CDCl$_3$, 300 MHz): 1.12 (t, 3H, Me), 2.20 (q, 2H, CH$_2$), 3.84 (s, 3H, OMe), 4.58 (s, 2H, CH$_2$OH), 4.69 (d, 2H, OCH$_2$C≡C), 6.82–7.01 (m, 3H, ar).

b) 4-Chloromethyl-2-methoxy-1-tent-2-ynyloxy-benzene

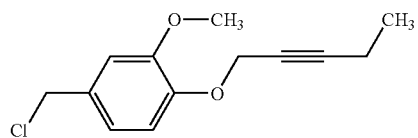

A solution of (3-methoxy-4-pent-2-ynyloxy-phenyl)-methanol (27 g, 0.12 mol) in 450 ml of dioxan is added dropwise to 240 ml of concentrated hydrochloric acid. The reaction mixture is stirred for 1.5 hours at room temperature. Subsequently it is poured on water and extracted with ethyl acetate. The combined organic layer is washed with brine, dried over magnesium sulfate and evaporated in vacuo to obtain 4-chloromethyl-2-methoxy-1-pent-2-ynyloxy-benzene as yellow oil.

$^1$H-NMR (CDCl$_3$, 300 MHz): 1.11 (t, 3H, Me), 2.21 (q, 2H, CH$_2$), 3.88 (s, 3H, OMe), 4.57 (s, 2H, CH$_2$Cl), 4.72 (d, 2H, OCH$_2$C≡C), 6.90–6.99 (m, 3H, ar).

c) 2-(3-Methoxy-4-pent-2-ynyloxy-benzyloxy)-isoindole-1,3-dione

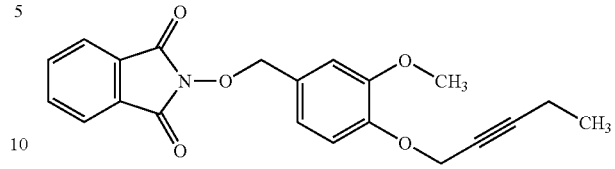

4-Chloromethyl-2-methoxy-1-pent-2-ynyloxy-benzene (28 g, 0.12 mol) and N-hydroxyphthalimide (19.5 g, 0.12 mol) are dissolved in 180 ml of N,N-dimethylformamide. The reaction mixture is heated to +70° C. and potassium hydroxide (24 ml of a 5 M solution in methanol, 0.12 mol) is added at this temperature. The reaction is stirred for 1 hour at +70° C., subsequently cooled to room temperature and poured on water. This mixture is stirred for one further hour and filtered. The resulting crystalls are washed with water and recrystallized from methanol/acetone (8:1) to yield 2-(3-methoxy-4-pent-2-ynyloxy-benzyloxy)-isoindole-1,3-dione as colourless crystals.

$^1$H-NMR (CDCl$_3$, 300 MHz): 1.09 (t, 3H, Me), 2.19 (q, 2H, CH$_2$), 3.90 (s, 3H, OMe), 4.72 (d, 2H, OCH$_2$C≡C), 5.18 (s, 2H, CH$_2$ON), 6.97–7.82 (m, 7H, ar).

d) O-(3-Methoxy-4-pent-2-ynyloxy-benzyl)-hydroxylamine

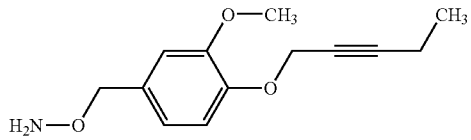

2-(3-Methoxy-4-pent-2-ynyloxy-benzyloxy)-isoindole-1,3-dione (27 g, 74 mmol) is suspended in a mixture of 500 ml of methanol and 50 ml of N,N-dimethylformamide. After heating this mixture to +60° C., hydrazine hydrate (8.5 g, 0.17 mol) is added. The reaction is stirred for 3 hours at +60° C. and subsequently cooled down to room temperature. A mixture of 28 ml of concentrated hydrochloric acid and 80 ml of water is added to acidify the resulting suspension. Then it is filtered to remove a precipitation and the solid is washed with water/methanol. The filtrate is concentrated in vacuo to one third of its original volume. Sodium hydroxide (18 g, mol in 90 ml water) is added to the remainder and this mixture is extracted with diethyl ether. The combined organic layer is washed with water and brine, dried over magnesium sulfate and evaporated to give O-(3-methoxy-4-pent-2-ynyloxy-benzyl)-hydroxylamine as yellow oil.

$^1$H-NMR (CDCl$_3$, 300 MHz): 1.10 (t, 3H, Me), 2.21 (q, 2H, CH$_2$), 3.88 (s, 3H, OMe), 4.65 (d, 2H, OCH$_2$C≡C), 4.73 (s, 2H, CH$_2$ON), 6.83–7.01 (m, 3H, ar).

e) O-(3-methoxy-4-pent-2-ynyloxy-benzyl)-hydroxylamine (5.0 g, 21 mmol) and N-ethyldiisopropylamine (Hünig's base, 5.5 g, 42 mmol) are dissolved in 60 ml of N,N-dimethylformamide. 4-chloro-DL-mandelic acid (4.1 g, 22 mmol) and (benzotriazol-1-yloxy)-tris-(dimethylamino)-phosphonium hexafluorophosphate (BOP, Castro's reagent, 10 g, 23 mmol) are added successively and the mixture is stirred for 16 h. After pouring the mixture on ice/water, it is extracted with ethyl acetate. The combined organic layer is washed with brine, dried over magnesium sulfate and evaporated under reduced pressure. The remaining oil is purified by chromatography on silica gel (ethyl acetate/hexane (4:6)) to obtain 2-(4-chloro-phenyl)-2-hydroxy-N-(3-methoxy-4-pent-2-ynyloxy-benzyloxy)-acetamide as yellow resin.

$^1$H-NMR (CDCl$_3$, 300 MHz): 1.12 (t, 3H, Me), 2.19 (q, 2H, CH$_2$), 3.83 (s, 3H, OMe), 4.69–4.78 (m, 4H, OCH$_2$C≡C, CH$_2$ON), 5.03 (s, 1H, CHOH), 6.72–7.33 (m, 7H, ar).

According to the example A1.1 described above the compounds listed in table A1 are obtained.

TABLE A1

| No. | R$_1$ | R$_8$ | physico-chemical data |
|---|---|---|---|
| A1.01 | 4-Cl—Ph- | 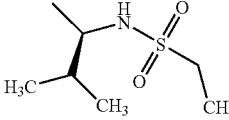 | m.p. 99–102 |
| A1.02 | H | 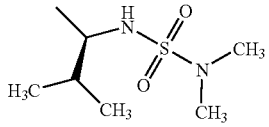 | m.p. 142–145 |
| A1.03 | 4-Cl—Ph— | 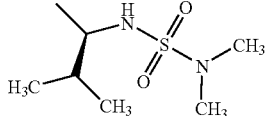 | m.p. 149–151 |
| A1.04 | H— | 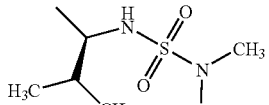 | Oil |
| A1.05 | CH$_3$—CH$_2$— | 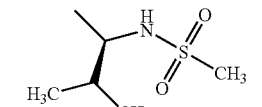 | m.p. 96–98 |
| A1.06 | CH$_3$—CH$_2$— | 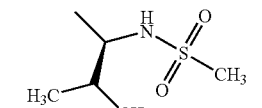 | m.p. 132–133 |
| A1.07 | 4-Cl—Ph— | 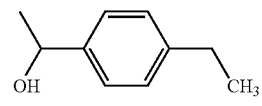 | m.p. 147–150 |
| A1.08 | H— | 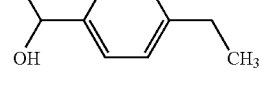 | Oil |
| A1.09 | CH$_3$—CH$_2$— | 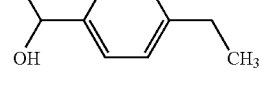 | Oil |

TABLE A1-continued

| No. | R₁ | R₈ | physico-chemical data |
|---|---|---|---|
| A1.10 | CH₃—CH₂— | 4-Cl-C₆H₄-CH(CH₃)-O-CH₂-C≡CH | Oil |
| A1.11 | H— | 4-Cl-C₆H₄-CH(OH)-CH₃ | Oil |
| A1.12 | CH₃—CH₂— | C₆H₅-CH(CH₃)-O-CH₂-C≡CH | Oil |
| A1.13 | CH₃—CH₂— | 4-Cl-C₆H₄-CH(OH)-CH₃ | Oil |
| A1.14 | H— | C₆H₅-CH(CH₃)-O-CH₂-C≡CH | m.p. 118–120 |
| A1.15 | H— | 4-Br-C₆H₄-CH(OH)-CH₃ | Oil |
| A1.16 | CH₃—CH₂— | 4-Br-C₆H₄-CH(OH)-CH₃ | Oil |
| A1.17 | CH₃—CH₂— | 3,4-Cl₂-C₆H₃-CH(OH)-CH₃ | Oil |
| A1.18 | H— | 4-Cl-C₆H₄-CH(CH₃)-O-CH₂-C≡CH | m.p. 125–127 |

Example A2.1

Hydroxy-(4-methoxy-phenyl)-acetic acid N'-(3-methoxy-4-prop-2-ynyloxy-benzyl)-hydrazide

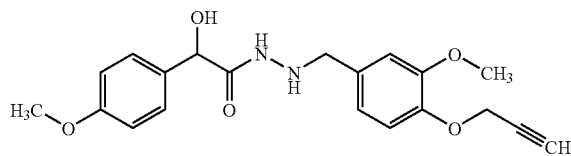

a) Hydroxy-(4-methoxy-phenyl)-acetic acid hydrazide

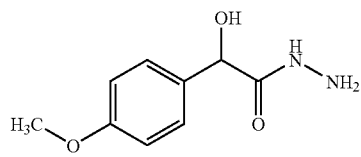

To a solution of hydroxy-(4-methoxy-phenyl)-acetic acid (45 g, 0.25 mol) in 300 ml of methanol are added 30 drops of concentrated sulfuric acid at room temperature and the resulting mixture is heated to reflux for 4 hours. Subsequently the mixture is cooled and evaporated in vacuo. The remainder is taken up in water and extracted with ethyl acetate. The combined organic layer isn washed with brine, dried over magnesium sulfate and evaporated. The residue, which is hydroxy-(4-methoxy-phenyl)-acetic acid methyl ester, is dissolved in 350 ml of diethyl ether. Hydrazine monohydrate (47 ml, 0.95 mol) is added dropwise at room temperature and the mixture is stirred for 1 hour. The reaction mixture is poured on water and extracted with ethyl acetate. The combined organic layer is washed with brine, dried over magnesium sulfate and evaporated, the remaining hydroxy-(4-methoxy-phenyl)-acetic acid hydrazide is sufficiently pure to be used directly in the next step.

$^1$H-NMR (CDCl$_3$, 300 MHz): 3.79 (s, 3H, OMe), 4.92 (d, 1H, CHOH), 5.91 (d, 1H, OH), 6.92 (d, 2H, ar), 7.36 (d, 2H, ar).

b) Hydroxy-(4-methoxy-phenyl)-acetic acid [1-(4-hydroxy-3-methoxy-phenyl)-meth-(E)-ylidene]-hydrazide

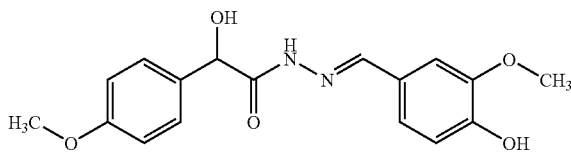

Vanillin (23 g, 0.15 mol) is added to a solution of hydroxy-(4-methoxy-phenyl)-acetic acid hydrazide (30 g, 0.15 mol) in 300 ml of ethanol at room temperature. After heating this mixture to reflux for 4 hours, the reaction is poured on water and extracted with ethyl acetate. The combined organic layer is washed with brine, dried over magnesium sulfate and evaporated. The residue, which is hydroxy-(4-methoxy-phenyl)-acetic acid [1-(4-hydroxy-3-methoxy-phenyl)-meth-(E)-ylidene]-hydrazide, is sufficiently pure to be directly used in the next step.

$^1$H-NMR (CDCl$_3$, 300 MHz): 3.72 (s, 3H, OMe), 3.80 (s, 3H, OMe), 4.99 (s, 1H, CHOH), 6.21 (d, 1H, CH=N), 6.79–7.42 (m, 7H, ar).

c) Hydroxy-(4-methoxy-phenyl)-acetic acid N'-(4-hydroxy-3-methoxy-benzyl)-hydrazide

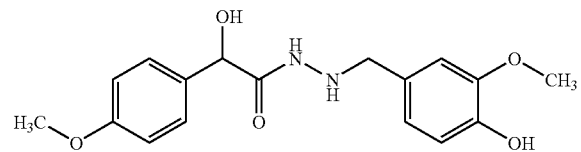

A solution of hydroxy-(4-methoxy-phenyl)-acetic acid [1-(4-hydroxy-3-methoxy-phenyl)-meth-(E)-ylidene]-hydrazide (21 g, 63 mmol) in 500 ml of ethanol is hydrogenated under atmospheric pressure with hydrogen and a mixture of 5% of palladium on charcoal (10.5 g) as catalyst. The reaction is stirred for 6 hours at room temperature. Subsequently, the mixture is filtered under argon and the solvent is evaporated to yield hydroxy-(4-methoxy-phenyl)-acetic acid N'-(4-hydroxy-3-methoxy-benzyl)-hydrazide as colourless tarr.

$^1$H-NMR (CDCl$_3$, 300 MHz): 3.56 (s, 3H, OMe), 3.63 (s, 3H, OMe), 3.71 (d, 2H, CH$_2$N), 4.73 (s, 1H, CHOH), 6.55–6.19 (m, 7H, ar).

d) A 80% propargyl bromide solution in toluene (2.1 g, 14.5 mmol) is added slowly at room temperature to a mixture of hydroxy-(4-methoxy-phenyl)-acetic acid N'-(4-hydroxy-3-methoxy-benzyl)-hydrazide (4.0 g, 12 mmol), 30% sodium hydroxide solution (3.5 ml, 14.5 mmol) and catalytic amounts of tetrabutylammonium bromide in 35 ml of dichloromethane. The reaction is stirred for 16 hours at +40° C. Subsequently the mixture is evaporated and the residue is diluted with water and dichloromethane. The phases are separated and the aqueous phase is extracted three times with dichloromethane. The combined organic phase is washed with brine, dried over sodium sulfate and evaporated. The remaining oil is purified by chromatography on silica gel (ethyl acetate/hexane 7:3) to obtain hydroxy-(4-methoxy-phenyl)-acetic acid N'-(3-methoxy-4-prop-2-ynyloxy-benzyl)-hydrazide.

$^1$H-NMR (CDCl$_3$, 300 MHz): 2.35 (dt, 1H, C≡CH), 3.79 (s, 3H, OMe), 3.82 (s, 3H, OMe), 3.91 (d, 2H, CH$_2$N), 4.78 (d, 2H, OCH$_2$C≡C), 4.93 (s, 1H, CHOH), 6.70–7.26 (m, 7H, ar).

According to the example A2.1 described above the compounds listed in table A2 are obtained.

TABLE A2

| No. | R$_1$ | R$_8$ | physico-chemical data |
|---|---|---|---|
| A2.01 | H | ![structure with OH, CH3 and 4-Cl-phenyl] | Oil |

TABLE A2-continued

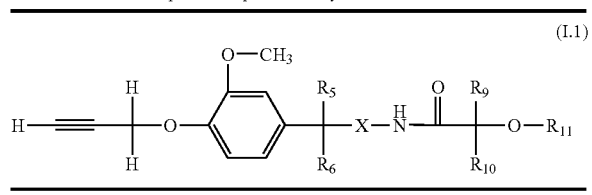

| No. | $R_1$ | $R_8$ | physico-chemical data |
|---|---|---|---|
| A2.02 | $CH_3-CH_2-$ | 1-(4-chlorophenyl)ethanol group | Oil |
| A2.03 | H | 1-(4-methylphenyl)ethanol group | Oil |
| A2.04 | $CH_3-CH_2-$ | 1-(4-methylphenyl)ethanol group | Oil |
| A2.05 | H | 1-(4-methoxyphenyl)ethanol group | Oil |
| A2.06 | $CH_3-CH_2-$ | 1-(4-methoxyphenyl)ethanol group | Oil |
| A2.07 | H | 1-phenylethanol group | Oil |
| A2.08 | $CH_3-CH_2-$ | 1-phenylethanol group | Oil |

Analogously to the above examples the compounds of tables 1 to 30 are obtained. Ph stands for phenyl

TABLE 1

Compounds represented by the Formula I.1

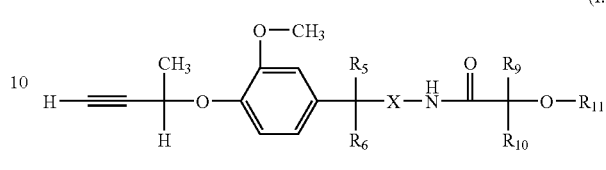

(I.1)

wherein the combination of the groups $R_5$, $R_6$, $R_9$, $R_{10}$, $R_{11}$ and X corresponds each to one row in table A.

TABLE 2

Compounds represented by the Formula I.2

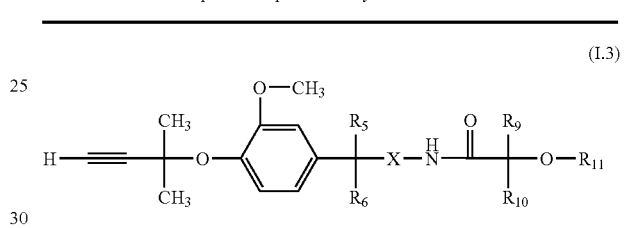

(I.2)

wherein the combination of the groups $R_5$, $R_6$, $R_9$, $R_{10}$, $R_{11}$, and X corresponds each to one row in table A.

TABLE 3

Compounds represented by the Formula I.3

(I.3)

wherein the combination of the groups $R_5$, $R_6$, $R_9$, $R_{10}$, $R_{11}$ and X corresponds each to one row in table A.

TABLE 4

Compounds represented by the Formula I.4

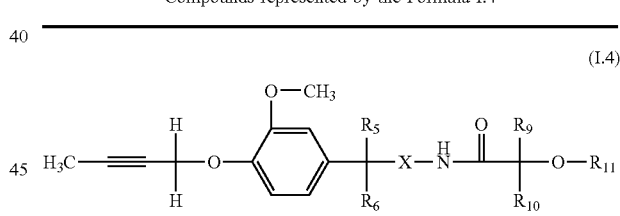

(I.4)

wherein the combination of the groups $R_5$, $R_6$, $R_9$, $R_{10}$, $R_{11}$ and X corresponds each to one row in table A.

TABLE 5

Compounds represented by the Formula I.5

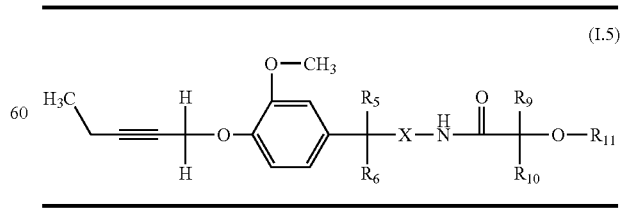

(I.5)

wherein the combination of the groups $R_5$, $R_6$, $R_9$, $R_{10}$, $R_{11}$ and X corresponds each to one row in table A.

TABLE 6

Compounds represented by the Formula I.6

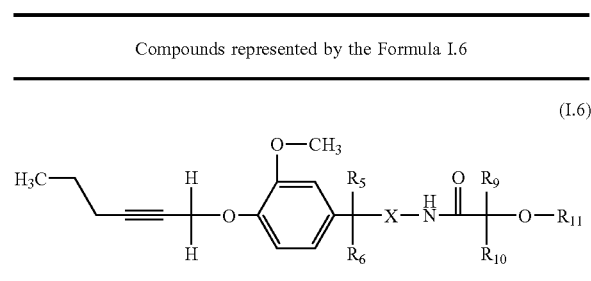

(I.6)

wherein the combination of the groups $R_5$, $R_6$, $R_9$, $R_{10}$, $R_{11}$, and X corresponds each to one row in table A.

TABLE 7

Compounds represented by the Formula I.7

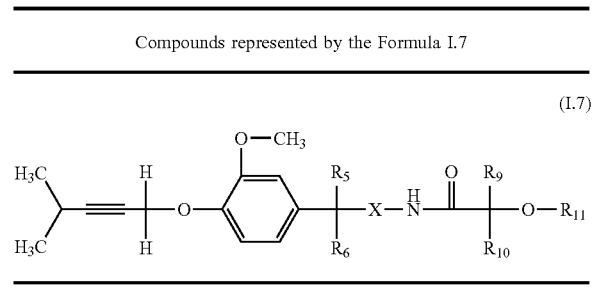

(I.7)

wherein the combination of the groups $R_5$, $R_6$, $R_9$, $R_{10}$, $R_{11}$ and X corresponds each to one row in table A.

TABLE 8

Compounds represented by the Formula I.8

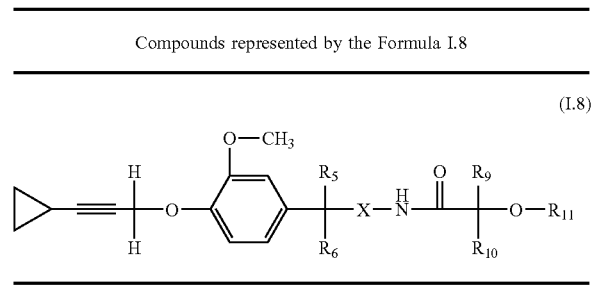

(I.8)

wherein the combination of the groups $R_5$, $R_6$, $R_9$, $R_{10}$, $R_{11}$ and X corresponds each to one row in table A.

TABLE 9

Compounds represented by the Formula I.9

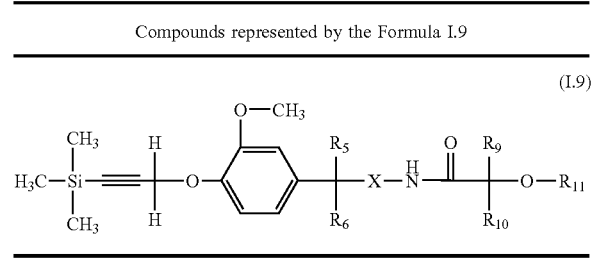

(I.9)

wherein the combination of the groups $R_5$, $R_6$, $R_9$, $R_{10}$, $R_{11}$ and X corresponds each to one row in table A.

TABLE 10

Compounds represented by the Formula I.10

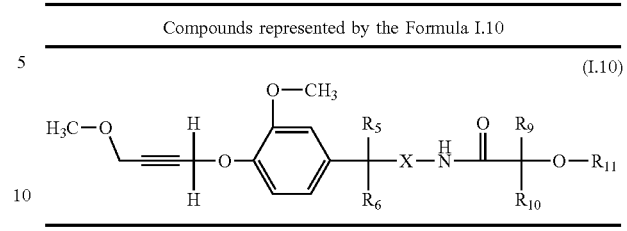

(I.10)

wherein the combination of the groups $R_5$, $R_6$, $R_9$, $R_{10}$, $R_{11}$ and X corresponds each to one table A.

TABLE A (Ph stands for phenyl):

| No. | $R_5$ | $R_6$ | X | $R_9$ | $R_{10}$ | $R_{11}$ |
|---|---|---|---|---|---|---|
| 001 | H | H | O | Ph | H | H |
| 002 | H | H | O | Ph | H | $CH_3$ |
| 003 | H | H | O | Ph | H | $CH_2CH_3$ |
| 004 | H | H | O | Ph | H | $CH_2C{\equiv}CH$ |
| 005 | $CH_3$ | H | O | Ph | H | $CH_2C{\equiv}CH$ |
| 006 | H | H | O | Ph | $CH_3$ | $CH_2C{\equiv}CH$ |
| 007 | H | H | NH | Ph | H | H |
| 008 | H | H | NH | Ph | H | $CH_3$ |
| 009 | H | H | NH | Ph | H | $CH_2CH_3$ |
| 010 | H | H | NH | Ph | H | $CH_2C{\equiv}CH$ |
| 011 | $CH_3$ | H | NH | Ph | H | $CH_2C{\equiv}CH$ |
| 012 | H | H | NH | Ph | $CH_3$ | $CH_2C{\equiv}CH$ |
| 013 | H | H | $NCH_3$ | Ph | H | H |
| 014 | H | H | $NCH_3$ | Ph | H | $CH_3$ |
| 015 | H | H | $NCH_3$ | Ph | H | $CH_2CH_3$ |
| 016 | H | H | $NCH_3$ | Ph | H | $CH_2C{\equiv}CH$ |
| 017 | $CH_3$ | H | $NCH_3$ | Ph | H | $CH_2C{\equiv}CH$ |
| 018 | H | H | $NOH_3$ | Ph | $CH_3$ | $CH_2C{\equiv}CH$ |
| 019 | H | H | O | 4-F—Ph | H | H |
| 020 | H | H | O | 4-F—Ph | H | $CH_3$ |
| 021 | H | H | O | 4-F—Ph | H | $CH_2CH_3$ |
| 022 | H | H | O | 4-F—Ph | H | $CH_2C{\equiv}CH$ |
| 023 | $CH_3$ | H | O | 4-F—Ph | H | $CH_2C{\equiv}CH$ |
| 024 | H | H | O | 4-F—Ph | $CH_3$ | $CH_2C{\equiv}CH$ |
| 025 | H | H | NH | 4-F—Ph | H | H |
| 026 | H | H | NH | 4-F—Ph | H | $CH_3$ |
| 027 | H | H | NH | 4-F—Ph | H | $CH_2CH_3$ |
| 028 | H | H | NH | 4-F—Ph | H | $CH_2C{\equiv}CH$ |
| 029 | $CH_3$ | H | NH | 4-F—Ph | H | $CH_2C{\equiv}CH$ |
| 030 | H | H | NH | 4-F—Ph | $CH_3$ | $CH_2C{\equiv}CH$ |
| 031 | H | H | $NCH_3$ | 4-F—Ph | H | H |
| 032 | H | H | $NCH_3$ | 4-F—Ph | H | $CH_3$ |
| 033 | H | H | $NCH_3$ | 4-F—Ph | H | $CH_2CH_3$ |
| 034 | H | H | $NCH_3$ | 4-F—Ph | H | $CH_2C{\equiv}CH$ |
| 035 | $CH_3$ | H | $NCH_3$ | 4-F—Ph | H | $CH_2C{\equiv}CH$ |
| 036 | H | H | $NCH_3$ | 4-F—Ph | $CH_3$ | $CH_2C{\equiv}CH$ |
| 037 | H | H | O | 4-Cl—Ph | H | H |
| 038 | H | H | O | 4-Cl—Ph | H | $CH_3$ |
| 039 | H | H | O | 4-Cl—Ph | H | $CH_2CH_3$ |
| 040 | H | H | O | 4-Cl—Ph | H | $CH_2C{\equiv}CH$ |
| 041 | $CH_3$ | H | O | 4-Cl—Ph | H | $CH_2C{\equiv}CH$ |
| 042 | H | H | O | 4-Cl—Ph | $CH_3$ | $CH_2C{\equiv}CH$ |
| 043 | H | H | NH | 4-Cl—Ph | H | H |
| 044 | H | H | NH | 4-Cl—Ph | H | $CH_3$ |
| 045 | H | H | NH | 4-Cl—Ph | H | $CH_2CH_3$ |
| 046 | H | H | NH | 4-Cl—Ph | H | $CH_2C{\equiv}CH$ |
| 047 | $CH_3$ | H | NH | 4-Cl—Ph | H | $CH_2C{\equiv}CH$ |
| 048 | H | H | NH | 4-Cl—Ph | $CH_3$ | $CH_2C{\equiv}CH$ |
| 049 | H | H | $NCH_3$ | 4-Cl—Ph | H | H |
| 050 | H | H | $NCH_3$ | 4-Cl—Ph | H | $CH_3$ |
| 051 | H | H | $NCH_3$ | 4-Cl—Ph | H | $CH_2CH_3$ |
| 052 | H | H | $NCH_3$ | 4-Cl—Ph | H | $CH_2C{\equiv}CH$ |
| 053 | $CH_3$ | H | $NCH_3$ | 4-Cl—Ph | H | $CH_2C{\equiv}CH$ |
| 054 | H | H | $NCH_3$ | 4-Br—Ph | $CH_3$ | $CH_2C{\equiv}CH$ |
| 055 | H | H | O | 4-Br—Ph | H | H |
| 056 | H | H | O | 4-Br—Ph | H | $CH_3$ |
| 057 | H | H | O | 4-Br—Ph | H | $CH_2CH_3$ |

TABLE A-continued (Ph stands for phenyl):

| No. | R$_5$ | R$_6$ | X | R$_9$ | R$_{10}$ | R$_{11}$ |
|---|---|---|---|---|---|---|
| 058 | H | H | O | 4-Br—Ph | H | CH$_2$C≡CH |
| 059 | CH$_3$ | H | O | 4-Br—Ph | H | CH$_2$C≡CH |
| 060 | H | H | O | 4-Br—Ph | CH$_3$ | CH$_2$C≡CH |
| 061 | H | H | NH | 4-Br—Ph | H | H |
| 062 | H | H | NH | 4-Br—Ph | H | CH$_3$ |
| 063 | H | H | NH | 4-Br—Ph | H | CH$_2$CH$_3$ |
| 064 | H | H | NH | 4-Br—Ph | H | CH$_2$C≡CH |
| 065 | CH$_3$ | H | NH | 4-Br—Ph | H | CH$_2$C≡CH |
| 066 | H | H | NH | 4-Br—Ph | CH$_3$ | CH$_2$C≡CH |
| 067 | H | H | NCH$_3$ | 4-Br—Ph | H | H |
| 068 | H | H | NCH$_3$ | 4-Br—Ph | H | CH$_3$ |
| 069 | H | H | NCH$_3$ | 4-Br—Ph | H | CH$_2$CH$_3$ |
| 070 | H | H | NCH$_3$ | 4-Br—Ph | H | CH$_2$C≡CH |
| 071 | CH$_3$ | H | NCH$_3$ | 4-Br—Ph | H | CH$_2$C≡CH |
| 072 | H | H | NCH$_3$ | 4-Br—Ph | CH$_3$ | CH$_2$C≡CH |
| 073 | H | H | O | 4-CH$_3$—Ph | H | H |
| 074 | H | H | O | 4-CH$_3$—Ph | H | CH$_3$ |
| 075 | H | H | O | 4-CH$_3$—Ph | H | CH$_2$CH$_3$ |
| 076 | H | H | O | 4-CH$_3$—Ph | H | CH$_2$C≡CH |
| 077 | CH$_3$ | H | O | 4-CH$_3$—Ph | H | CH$_2$C≡CH |
| 078 | H | H | O | 4-CH$_3$—Ph | CH$_3$ | CH$_2$C≡CH |
| 079 | H | H | NH | 4-CH$_3$—Ph | H | H |
| 080 | H | H | NH | 4-CH$_3$—Ph | H | CH$_3$ |
| 081 | H | H | NH | 4-CH$_3$—Ph | H | CH$_2$CH$_3$ |
| 082 | H | H | NH | 4-CH$_3$—Ph | H | CH$_2$C≡CH |
| 083 | CH$_3$ | H | NH | 4-CH$_3$—Ph | H | CH$_2$C≡CH |
| 084 | H | H | NH | 4-CH$_3$—Ph | CH$_3$ | CH$_2$C≡CH |
| 085 | H | H | NCH$_3$ | 4-CH$_3$—Ph | H | H |
| 086 | H | H | NCH$_3$ | 4-CH$_3$—Ph | H | CH$_3$ |
| 087 | H | H | NCH$_3$ | 4-CH$_3$—Ph | H | CH$_2$CH$_3$ |
| 088 | H | H | NCH$_3$ | 4-CH$_3$—Ph | H | CH$_2$C≡CH |
| 089 | CH$_3$ | H | NCH$_3$ | 4-CH$_3$—Ph | H | CH$_2$C≡CH |
| 090 | H | H | NCH$_3$ | 4-CH$_3$—Ph | CH$_3$ | CH$_2$C≡CH |
| 091 | H | H | O | 4-CH$_3$CH$_2$—Ph | H | H |
| 092 | H | H | O | 4-CH$_3$CH$_2$—Ph | H | CH$_3$ |
| 093 | H | H | O | 4-CH$_3$CH$_2$—Ph | H | CH$_2$CH$_3$ |
| 094 | H | H | O | 4-CH$_3$CH$_2$—Ph | H | CH$_2$C≡CH |
| 095 | CH$_3$ | H | O | 4-CH$_3$CH$_2$—Ph | H | CH$_2$C≡CH |
| 096 | H | H | O | 4-CH$_3$CH$_2$—Ph | CH$_3$ | CH$_2$C≡CH |
| 097 | H | H | NH | 4-CH$_3$CH$_2$—Ph | H | H |
| 098 | H | H | NH | 4-CH$_3$CH$_2$—Ph | H | CH$_3$ |
| 099 | H | H | NH | 4-CH$_3$CH$_2$—Ph | H | CH$_2$CH$_3$ |
| 100 | H | H | NH | 4-CH$_3$CH$_2$—Ph | H | CH$_2$C≡CH |
| 101 | CH$_3$ | H | NH | 4-CH$_3$CH$_2$—Ph | H | CH$_2$C≡CH |
| 102 | H | H | NH | 4-CH$_3$CH$_2$—Ph | CH$_3$ | CH$_2$C≡CH |
| 103 | H | H | NCH$_3$ | 4-CH$_3$CH$_2$—Ph | H | H |
| 104 | H | H | NCH$_3$ | 4-CH$_3$CH$_2$—Ph | H | CH$_3$ |
| 105 | H | H | NCH$_3$ | 4-CH$_3$CH$_2$—Ph | H | CH$_2$CH$_3$ |
| 106 | H | H | NCH$_3$ | 4-CH$_3$CH$_2$—Ph | H | CH$_2$C≡CH |
| 107 | CH$_3$ | H | NCH$_3$ | 4-CH$_3$CH$_2$—Ph | H | CH$_2$C≡CH |
| 108 | H | H | NCH$_3$ | 4-CH$_3$CH$_2$—Ph | CH$_3$ | CH$_2$C≡CH |
| 109 | H | H | O | 4-CF$_3$—Ph | H | H |
| 110 | H | H | O | 4-CF$_3$—Ph | H | CH$_3$ |
| 111 | H | H | O | 4-CF$_3$—Ph | H | CH$_2$CH$_3$ |
| 112 | H | H | O | 4-CF$_3$—Ph | H | CH$_2$C≡CH |
| 113 | CH$_3$ | H | O | 4-CF$_3$—Ph | H | CH$_2$C≡CH |
| 114 | H | H | O | 4-CF$_3$—Ph | CH$_3$ | CH$_2$C≡CH |
| 115 | H | H | NH | 4-CF$_3$—Ph | H | H |
| 116 | H | H | NH | 4-CF$_3$—Ph | H | CH$_3$ |
| 117 | H | H | NH | 4-CF$_3$—Ph | H | CH$_2$CH$_3$ |
| 118 | H | H | NH | 4-CF$_3$—Ph | H | CH$_2$C≡CH |
| 119 | CH$_3$ | H | NH | 4-CF$_3$—Ph | H | CH$_2$C≡CH |
| 120 | H | H | NH | 4-CF$_3$—Ph | CH$_3$ | CH$_2$C≡CH |
| 121 | H | H | NCH$_3$ | 4-CF$_3$—Ph | H | H |
| 122 | H | H | NCH$_3$ | 4-CF$_3$—Ph | H | CH$_3$ |
| 123 | H | H | NCH$_3$ | 4-CF$_3$—Ph | H | CH$_2$CH$_3$ |
| 124 | H | H | NCH$_3$ | 4-CF$_3$—Ph | H | CH$_2$C≡CH |
| 125 | CH$_3$ | H | NCH$_3$ | 4-CF$_3$—Ph | H | CH$_2$C≡CH |
| 126 | H | H | NCH$_3$ | 4-CF$_3$—Ph | CH$_3$ | CH$_2$C≡CH |
| 127 | H | H | O | 4-CH$_3$O—Ph | H | H |
| 128 | H | H | O | 4-CH$_3$O—Ph | H | CH$_3$ |
| 129 | H | H | O | 4-CH$_3$O—Ph | H | CH$_2$CH$_3$ |
| 130 | H | H | O | 4-CH$_3$O—Ph | H | CH$_2$C≡CH |
| 131 | CH$_3$ | H | O | 4-CH$_3$O—Ph | H | CH$_2$C≡CH |
| 132 | H | H | O | 4-CH$_3$O—Ph | CH$_3$ | CH$_2$C≡CH |
| 133 | H | H | NH | 4-CH$_3$O—Ph | H | H |
| 134 | H | H | NH | 4-CH$_3$O—Ph | H | CH$_3$ |
| 135 | H | H | NH | 4-CH$_3$O—Ph | H | CH$_2$CH$_3$ |
| 136 | H | H | NH | 4-CH$_3$O—Ph | H | CH$_2$C≡CH |
| 137 | CH$_3$ | H | NH | 4-CH$_3$O—Ph | H | CH$_2$C≡CH |
| 138 | H | H | NH | 4-CH$_3$O—Ph | CH$_3$ | CH$_2$C≡CH |
| 139 | H | H | NCH$_3$ | 4-CH$_3$O—Ph | H | H |
| 140 | H | H | NCH$_3$ | 4-CH$_3$O—Ph | H | CH$_3$ |
| 141 | H | H | NCH$_3$ | 4-CH$_3$O—Ph | H | CH$_2$CH$_3$ |
| 142 | H | H | NCH$_3$ | 4-CH$_3$O—Ph | H | CH$_2$C≡CH |
| 143 | CH$_3$ | H | NCH$_3$ | 4-CH$_3$O—Ph | H | CH$_2$C≡CH |
| 144 | H | H | NCH$_3$ | 4-CH$_3$O—Ph | CH$_3$ | CH$_2$C≡CH |
| 145 | H | H | O | 4-CF$_3$O—Ph | H | H |
| 146 | H | H | O | 4-CF$_3$O—Ph | H | CH$_3$ |
| 147 | H | H | O | 4-CF$_3$O—Ph | H | CH$_2$CH$_3$ |
| 148 | H | H | O | 4-CF$_3$O—Ph | H | CH$_2$C≡CH |
| 149 | CH$_3$ | H | O | 4-CF$_3$O—Ph | H | CH$_2$C≡CH |
| 150 | H | H | O | 4-CF$_3$O—Ph | CH$_3$ | CH$_2$C≡CH |
| 151 | H | H | NH | 4-CF$_3$O—Ph | H | H |
| 152 | H | H | NH | 4-CF$_3$O—Ph | H | CH$_3$ |
| 153 | H | H | NH | 4-CF$_3$O—Ph | H | CH$_2$CH$_3$ |
| 154 | H | H | NH | 4-CF$_3$O—Ph | H | CH$_2$C≡CH |
| 155 | CH$_3$ | H | NH | 4-CF$_3$O—Ph | H | CH$_2$C≡CH |
| 156 | H | H | NH | 4-CF$_3$O—Ph | CH$_3$ | CH$_2$C≡CH |
| 157 | H | H | NCH$_3$ | 4-CF$_3$O—Ph | H | H |
| 158 | H | H | NCH$_3$ | 4-CF$_3$O—Ph | H | CH$_3$ |
| 159 | H | H | NCH$_3$ | 4-CF$_3$O—Ph | H | CH$_2$CH$_3$ |
| 160 | H | H | NCH$_3$ | 4-CF$_3$O—Ph | H | CH$_2$C≡CH |
| 161 | CH$_3$ | H | NCH$_3$ | 4-CF$_3$O—Ph | H | CH$_2$C≡CH |
| 162 | H | H | NCH$_3$ | 4-CF$_3$O—Ph | CH$_3$ | CH$_2$C≡CH |
| 163 | H | H | O | 3,4-Cl$_2$—Ph | H | H |
| 164 | H | H | O | 3,4-Cl$_2$—Ph | H | CH$_3$ |
| 165 | H | H | O | 3,4-Cl$_2$—Ph | H | CH$_2$CH$_3$ |
| 166 | H | H | O | 3,4-Cl$_2$—Ph | H | CH$_2$C≡CH |
| 167 | CH$_3$ | H | O | 3,4-Cl$_2$—Ph | H | CH$_2$C≡CH |
| 168 | H | H | O | 3,4-Cl$_2$—Ph | CH$_3$ | CH$_2$C≡CH |
| 169 | H | H | NH | 3,4-Cl$_2$—Ph | H | H |
| 170 | H | H | NH | 3,4-Cl$_2$—Ph | H | CH$_3$ |
| 171 | H | H | NH | 3,4-Cl$_2$—Ph | H | CH$_2$CH$_3$ |
| 172 | H | H | NH | 3,4-Cl$_2$—Ph | H | CH$_2$C≡CH |
| 173 | CH$_3$ | H | NH | 3,4-Cl$_2$—Ph | H | CH$_2$C≡CH |
| 174 | H | H | NH | 3,4-Cl$_2$—Ph | CH$_3$ | CH$_2$C≡CH |
| 175 | H | H | NCH$_3$ | 3,4-Cl$_2$—Ph | H | H |
| 176 | H | H | NCH$_3$ | 3,4-Cl$_2$—Ph | H | CH$_3$ |
| 177 | H | H | NCH$_3$ | 3,4-Cl$_2$—Ph | H | CH$_2$CH$_3$ |
| 178 | H | H | NCH$_3$ | 3,4-Cl$_2$—Ph | H | CH$_2$C≡CH |
| 179 | CH$_3$ | H | NCH$_3$ | 3,4-Cl$_2$—Ph | H | CH$_2$C≡CH |
| 180 | H | H | NCH$_3$ | 3,4-Cl$_2$—Ph | CH$_3$ | CH$_2$C≡CH |
| 181 | H | H | O | 3,4-F$_2$—Ph | H | H |
| 182 | H | H | O | 3,4-F$_2$—Ph | H | CH$_3$ |
| 183 | H | H | O | 3,4-F$_2$—Ph | H | CH$_2$CH$_3$ |
| 184 | H | H | O | 3,4-F$_2$—Ph | H | CH$_2$C≡CH |
| 185 | CH$_3$ | H | O | 3,4-F$_2$—Ph | H | CH$_2$C≡CH |
| 186 | H | H | O | 3,4-F$_2$—Ph | CH$_3$ | CH$_2$C≡CH |
| 187 | H | H | NH | 3,4-F$_2$—Ph | H | H |
| 188 | H | H | NH | 3,4-F$_2$—Ph | H | CH$_3$ |
| 189 | H | H | NH | 3,4-F$_2$—Ph | H | CH$_2$CH$_3$ |
| 190 | H | H | NH | 3,4-F$_2$—Ph | H | CH$_2$C≡CH |
| 191 | CH$_3$ | H | NH | 3,4-F$_2$—Ph | H | CH$_2$C≡CH |
| 192 | H | H | NH | 3,4-F$_2$—Ph | CH$_3$ | CH$_2$C≡CH |
| 193 | H | H | NCH$_3$ | 3,4-F$_2$—Ph | H | H |
| 194 | H | H | NCH$_3$ | 3,4-F$_2$—Ph | H | CH$_3$ |
| 195 | H | H | NCH$_3$ | 3,4-F$_2$—Ph | H | CH$_2$CH$_3$ |
| 196 | H | H | NCH$_3$ | 3,4-F$_2$—Ph | H | CH$_2$C≡CH |
| 197 | CH$_3$ | H | NCH$_3$ | 3,4-F$_2$—Ph | H | CH$_2$C≡CH |
| 198 | H | H | NCH$_3$ | 3,4-F$_2$—Ph | CH$_3$ | CH$_2$C≡CH |
| 199 | H | H | O | 3-Cl-4-F—Ph | H | H |
| 200 | H | H | O | 3-Cl-4-F—Ph | H | CH$_3$ |
| 201 | H | H | O | 3-Cl-4-F—Ph | H | CH$_2$CH$_3$ |
| 202 | H | H | O | 3-Cl-4-F—Ph | H | CH$_2$C≡CH |
| 203 | CH$_3$ | H | O | 3-Cl-4-F—Ph | H | CH$_2$C≡CH |
| 204 | H | H | O | 3-Cl-4-F—Ph | CH$_3$ | CH$_2$C≡CH |
| 205 | H | H | NH | 3-Cl-4-F—Ph | H | H |
| 206 | H | H | NH | 3-Cl-4-F—Ph | H | CH$_3$ |
| 207 | H | H | NH | 3-Cl-4-F—Ph | H | CH$_2$CH$_3$ |

TABLE A-continued (Ph stands for phenyl):

| No. | R5 | R6 | X | R9 | R10 | R11 |
|---|---|---|---|---|---|---|
| 208 | H | H | NH | 3-Cl-4-F—Ph | H | CH$_2$C≡CH |
| 209 | CH$_3$ | H | NH | 3-Cl-4-F—Ph | H | CH$_2$C≡CH |
| 210 | H | H | NH | 3-Cl-4-F—Ph | CH$_3$ | CH$_2$C≡CH |
| 211 | H | H | NCH$_3$ | 3-Cl-4-F—Ph | H | H |
| 212 | H | H | NCH$_3$ | 3-Cl-4-F—Ph | H | CH$_3$ |
| 213 | H | H | NCH$_3$ | 3-Cl-4-F—Ph | H | CH$_2$CH$_3$ |
| 214 | H | H | NCH$_3$ | 3-Cl-4-F—Ph | H | CH$_2$C≡CH |
| 215 | CH$_3$ | H | NCH$_3$ | 3-Cl-4-F—Ph | H | CH$_2$C≡CH |
| 216 | H | H | NCH$_3$ | 3-Cl-4-F—Ph | CH$_3$ | CH$_2$C≡CH |
| 217 | H | H | O | 4-Cl-3-F—Ph | H | H |
| 218 | H | H | O | 4-Cl-3-F—Ph | H | CH$_3$ |
| 219 | H | H | O | 4-Cl-3-F—Ph | H | CH$_2$CH$_3$ |
| 220 | H | H | O | 4-Cl-3-F—Ph | H | CH$_2$C≡CH |
| 221 | CH$_3$ | H | O | 4-Cl-3-F—Ph | H | CH$_2$C≡CH |
| 222 | H | H | O | 4-Cl-3-F—Ph | CH$_3$ | CH$_2$C≡CH |
| 223 | H | H | NH | 4-Cl-3-F—Ph | H | H |
| 224 | H | H | NH | 4-Cl-3-F—Ph | H | CH$_3$ |
| 225 | H | H | NH | 4-Cl-3-F—Ph | H | CH$_2$CH$_3$ |
| 226 | H | H | NH | 4-Cl-3-F—Ph | H | CH$_2$C≡CH |
| 227 | CH$_3$ | H | NH | 4-Cl-3-F—Ph | H | CH$_2$C≡CH |
| 228 | H | H | NH | 4-Cl-3-F—Ph | CH$_3$ | CH$_2$C≡CH |
| 229 | H | H | NCH$_3$ | 4-Cl-3-F—Ph | H | H |
| 230 | H | H | NCH$_3$ | 4-Cl-3-F—Ph | H | CH$_3$ |
| 231 | H | H | NCH$_3$ | 4-Cl-3-F—Ph | H | CH$_2$CH$_3$ |
| 232 | H | H | NCH$_3$ | 4-Cl-3-F—Ph | H | CH$_2$C≡CH |
| 233 | CH$_3$ | H | NCH$_3$ | 4-Cl-3-F—Ph | H | CH$_2$C≡CH |
| 234 | H | H | NCH$_3$ | 4-Cl-3-F—Ph | CH$_3$ | CH$_2$C≡CH |
| 235 | H | H | O | 2-naphthyl | H | H |
| 236 | H | H | O | 2-naphthyl | H | CH$_3$ |
| 237 | H | H | O | 2-naphthyl | H | CH$_2$CH$_3$ |
| 238 | H | H | O | 2-naphthyl | H | CH$_2$C≡CH |
| 239 | CH$_3$ | H | O | 2-naphthyl | H | CH$_2$C≡CH |
| 240 | H | H | O | 2-naphthyl | CH$_3$ | CH$_2$C≡CH |
| 241 | H | H | NH | 2-naphthyl | H | H |
| 242 | H | H | NH | 2-naphthyl | H | CH$_3$ |
| 243 | H | H | NH | 2-naphthyl | H | CH$_2$CH$_3$ |
| 244 | H | H | NH | 2-naphthyl | H | CH$_2$C≡CH |
| 245 | CH$_3$ | H | NH | 2-naphthyl | H | CH$_2$C≡CH |
| 246 | H | H | NH | 2-naphthyl | CH$_3$ | CH$_2$C≡CH |
| 247 | H | H | NCH$_3$ | 2-naphthyl | H | H |
| 248 | H | H | NCH$_3$ | 2-naphthyl | H | CH$_3$ |
| 249 | H | H | NCH$_3$ | 2-naphthyl | H | CH$_2$CH$_3$ |
| 250 | H | H | NCH$_3$ | 2-naphthyl | H | CH$_2$C≡CH |
| 251 | CH$_3$ | H | NCH$_3$ | 2-naphthyl | H | CH$_2$C≡CH |
| 252 | H | H | NCH$_3$ | 2-naphthyl | CH$_3$ | CH$_2$C≡CH |
| 253 | H | H | O | 5,6,7,8-tetrahydro-2-naphthyl | H | H |
| 254 | H | H | O | 5,6,7,8-tetrahydro-2-naphthyl | H | CH$_3$ |
| 255 | H | H | O | 5,6,7,8-tetrahydro-2-naphthyl | H | CH$_2$CH$_3$ |

TABLE A-continued (Ph stands for phenyl):

| No. | R5 | R6 | X | R9 | R10 | R11 |
|---|---|---|---|---|---|---|
| 256 | H | H | O | 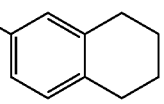 | H | CH₂C≡CH |
| 257 | CH₃ | H | O | 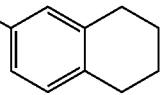 | H | CH₂C≡CH |
| 258 | H | H | O | 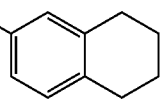 | CH₃ | CH₂C≡CH |
| 259 | H | H | NH | 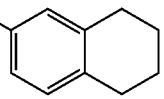 | H | H |
| 260 | H | H | NH | 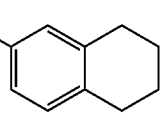 | H | CH₃ |
| 261 | H | H | NH | 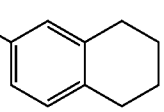 | H | CH₂CH₃ |
| 262 | H | H | NH | 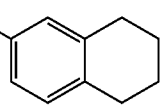 | H | CH₂C≡CH |
| 253 | CH₃ | H | NH | 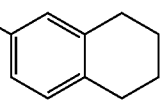 | H | CH₂C≡CH |
| 264 | H | H | NH | 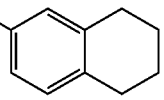 | CH₃ | CH₂C≡CH |
| 265 | H | H | NCH₃ | 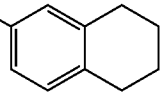 | H | H |
| 266 | H | H | NCH₃ | 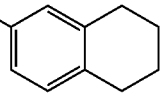 | H | CH₃ |
| 267 | H | H | NCH₃ | 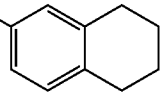 | H | CH₂CH₃ |
| 268 | H | H | NCH₃ | 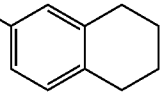 | H | CH₂C≡CH |
| 269 | CH₃ | H | NCH₃ | 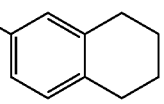 | H | CH₂C≡CH |
| 270 | H | H | NCH₃ | 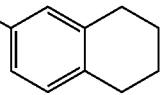 | CH₃ | CH₂C≡CH |
| 271 | H | H | O | 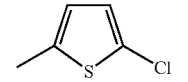 | H | H |
| 272 | H | H | O | 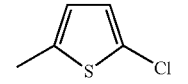 | H | CH₃ |
| 273 | H | H | O | 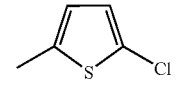 | H | CH₂CH₃ |
| 274 | H | H | O | 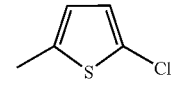 | H | CH₂C≡CH |
| 275 | CH₃ | H | O | 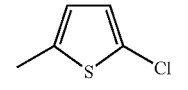 | H | CH₂C≡CH |
| 276 | H | H | O | 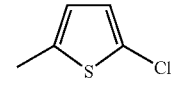 | CH₃ | CH₂C≡CH |
| 277 | H | H | NH | 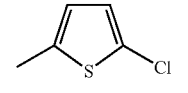 | H | H |
| 278 | H | H | NH | 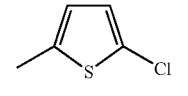 | H | CH₃ |
| 279 | H | H | NH | 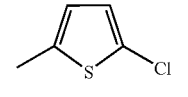 | H | CH₂CH₃ |
| 280 | H | H | NH | 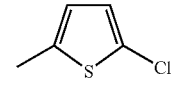 | H | CH₂C≡CH |
| 281 | CH₃ | H | NH | 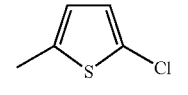 | H | CH₂C≡CH |
| 282 | H | H | NH | 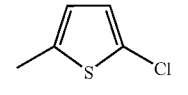 | CH₃ | CH₂C≡CH |
| 283 | H | H | NCH₃ | 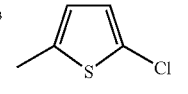 | H | H |

TABLE A-continued (Ph stands for phenyl):

| No. | $R_5$ | $R_6$ | X | $R_9$ | $R_{10}$ | $R_{11}$ |
|---|---|---|---|---|---|---|
| 284 | H | H | $NCH_3$ | 5-chloro-2-methylthiophene | H | $CH_3$ |
| 285 | H | H | $NCH_3$ | 5-chloro-2-methylthiophene | H | $CH_2CH_3$ |
| 286 | H | H | $NCH_3$ | 5-chloro-2-methylthiophene | H | $CH_2C{\equiv}CH$ |
| 287 | $CH_3$ | H | $NCH_3$ | 5-chloro-2-methylthiophene | H | $CH_2C{\equiv}CH$ |
| 288 | H | H | $NCH_3$ | 5-chloro-2-methylthiophene | $CH_3$ | $CH_2C{\equiv}CH$ |
| 289 | H | H | O | 6-chloro-3-pyridyl | H | H |
| 290 | H | H | O | 6-chloro-3-pyridyl | H | $CH_3$ |
| 291 | H | H | O | 6-chloro-3-pyridyl | H | $CH_2CH_3$ |
| 292 | H | H | O | 6-chloro-3-pyridyl | H | $CH_2C{\equiv}CH$ |
| 293 | $CH_3$ | H | O | 6-chloro-3-pyridyl | H | $CH_2C{\equiv}CH$ |
| 294 | H | H | O | 6-chloro-3-pyridyl | $CH_3$ | $CH_2C{\equiv}CH$ |
| 295 | H | H | NH | 6-chloro-3-pyridyl | H | H |
| 296 | H | H | NH | 6-chloro-3-pyridyl | H | $CH_3$ |
| 297 | H | H | NH | 6-chloro-3-pyridyl | H | $CH_2CH_3$ |
| 298 | H | H | NH | 6-chloro-3-pyridyl | H | $CH_2C{\equiv}CH$ |
| 299 | $CH_3$ | H | NH | 6-chloro-3-pyridyl | H | $CH_2C{\equiv}CH$ |
| 300 | H | H | NH | 6-chloro-3-pyridyl | $CH_3$ | $CH_2C{\equiv}CH$ |
| 301 | H | H | $NCH_3$ | 6-chloro-3-pyridyl | H | H |
| 302 | H | H | $NCH_3$ | 6-chloro-3-pyridyl | H | $CH_3$ |
| 303 | H | H | $NCH_3$ | 6-chloro-3-pyridyl | H | $CH_2CH_3$ |
| 304 | H | H | $NCH_3$ | 6-chloro-3-pyridyl | H | $CH_2C{\equiv}CH$ |
| 305 | $CH_3$ | H | $NCH_3$ | 6-chloro-3-pyridyl | H | $CH_2C{\equiv}CH$ |
| 306 | H | H | $NCH_3$ | 6-chloro-3-pyridyl | $CH_3$ | $CH_2C{\equiv}CH$ |

TABLE 11

Compounds represented by the Formula I.11

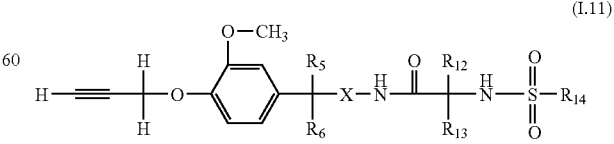

(I.11)

wherein the combination of the groups $R_5$, $R_6$, $R_{12}$, $R_{13}$, $R_{14}$ and X corresponds each to one row in table B.

TABLE 12

Compounds represented by the Formula I.12

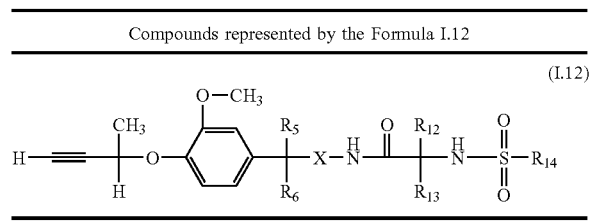

(I.12)

wherein the combination of the groups $R_5$, $R_6$, $R_{12}$, $R_{13}$, $R_{14}$ and X corresponds each to one row in table B.

TABLE 13

Compounds represented by the Formula I.13

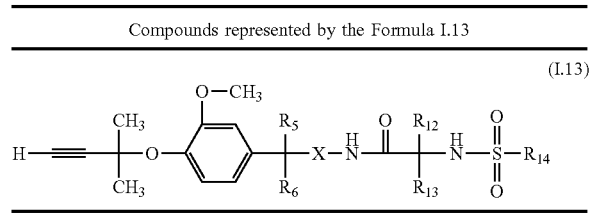

(I.13)

wherein the combination of the groups $R_5$, $R_6$, $R_{12}$, $R_{13}$, $R_{14}$ and X corresponds each to one row in table B.

TABLE 14

Compounds represented by the Formula I.14

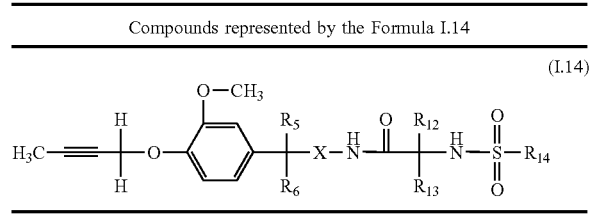

(I.14)

wherein the combination of the groups $R_5$, $R_6$, $R_{12}$, $R_{13}$, $R_{14}$ and X corresponds each to one row in table B.

TABLE 15

Compounds represented by the Formula I.15

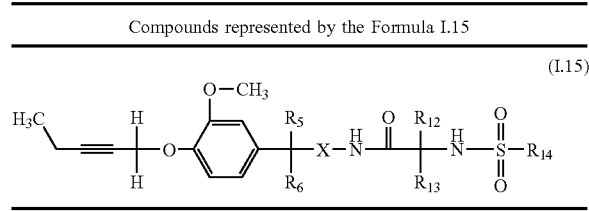

(I.15)

wherein the combination of the groups $R_5$, $R_6$, $R_{12}$, $R_{13}$, $R_{14}$ and X corresponds each to one row in table B.

TABLE 16

Compounds represented by the Formula I.16

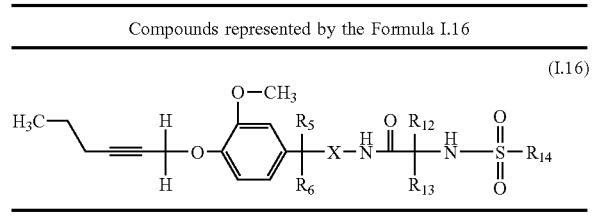

(I.16)

wherein the combination of the groups $R_5$ $R_6$, $R_{12}$, $R_{13}$, $R_{14}$ and X corresponds each to one row in table B.

TABLE 17

Compounds represented by the Formula I.17

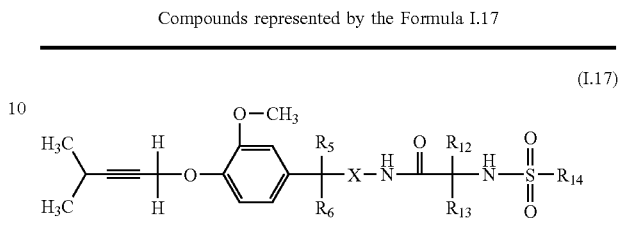

(I.17)

wherein the combination of the groups $R_5$, $R_6$, $R_{12}$, $R_{13}$, $R_{14}$ and X corresponds each to one row in table B.

TABLE 18

Compounds represented by the Formula I.18

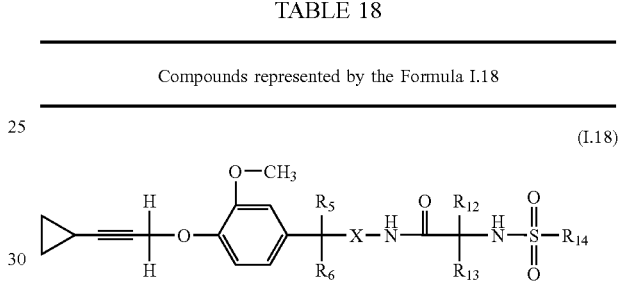

(I.18)

wherein the combination of the groups $R_5$, $R_6$, $R_{12}$, $R_{13}$, $R_{14}$ and X corresponds each to one row in table B.

TABLE 19

Compounds represented by the Formula I.19

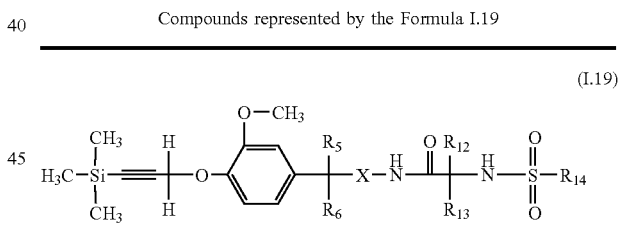

(I.19)

wherein the combination of the groups $R_5$, $R_6$, $R_{12}$, $R_{13}$, $R_{14}$ and X corresponds each to one row in table B.

TABLE 20

Compounds represented by the Formula I.20

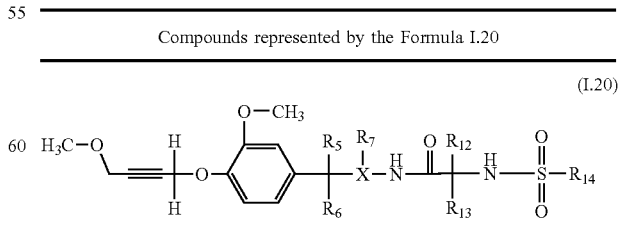

(I.20)

wherein the combination of the groups $R_5$, $R_6$, $R_{12}$, $R_{13}$, $R_{14}$ and X corresponds each to one row in table B.

TABLE 21

Compounds represented by the Formula I.21

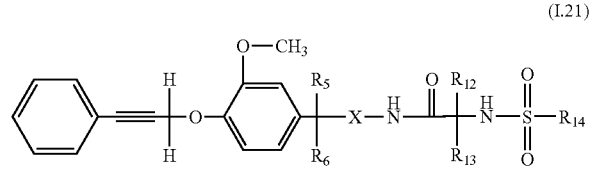

(I.21)

wherein the combination of the groups $R_5$, $R_6$, $R_{12}$, $R_{13}$, $R_{14}$ and X corresponds each to one row in table B.

TABLE 22

Compounds represented by the Formula I.22

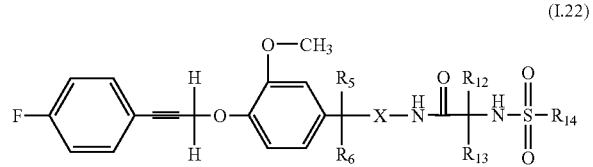

(I.22)

wherein the combination of the groups $R_5$, $R_6$, $R_{12}$, $R_{13}$, $R_{14}$ and X corresponds each to one row in table B.

TABLE 23

Compounds represented by the Formula I.23

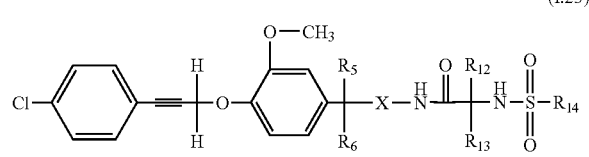

(I.23)

wherein the combination of the groups $R_5$, $R_6$, $R_{12}$, $R_{13}$, $R_{14}$ and X corresponds each to one row in table B.

TABLE 24

Compounds represented by the Formula I.24

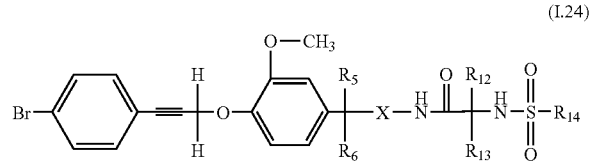

(I.24)

wherein the combination of the groups $R_5$, $R_6$, $R_{12}$, $R_{13}$, $R_{14}$ and X corresponds each to one row in table B.

TABLE 25

Compounds represented by the Formula I.25

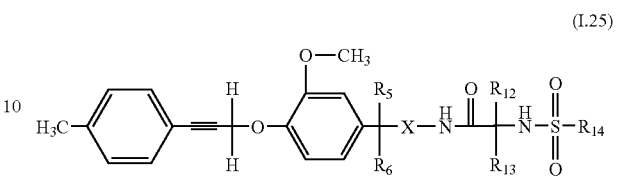

(I.25)

wherein the combination of the groups $R_5$, $R_6$, $R_{12}$, $R_{13}$, $R_{14}$ and X corresponds each to one row in table B.

TABLE 26

Compounds represented by the Formula I.26

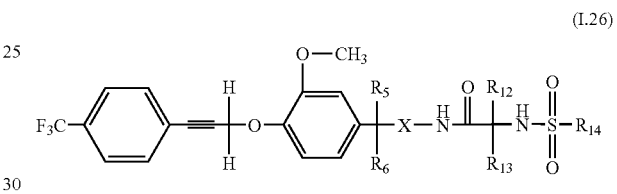

(I.26)

wherein the combination of the groups $R_5$ $R_6$, $R_{12}$, $R_{13}$, $R_{14}$ and X corresponds each to one row in table B.

TABLE 27

Compounds represented by the Formula I.27

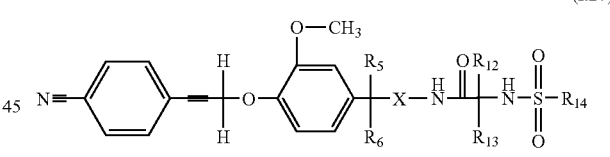

(I.27)

wherein the combination of the groups $R_5$, $R_6$, $R_{12}$, $R_{13}$, $R_{14}$ and X corresponds each to one row in table B.

TABLE 28

Compounds represented by the Formula I.28

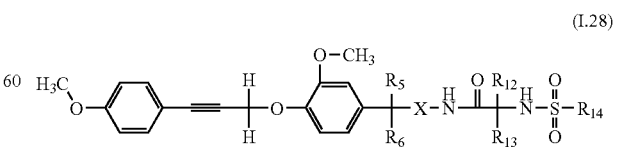

(I.28)

wherein the combination of the groups $R_5$ $R_6$, $R_{12}$, $R_{13}$, $R_{14}$ and X corresponds each to one row in table B.

TABLE 29

Compounds represented by the Formula I.29

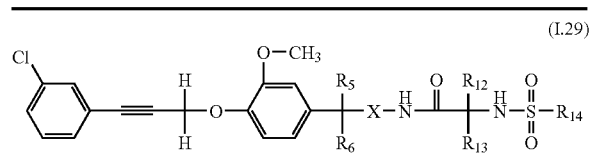

(I.29)

wherein the combination of the groups $R_5$, $R_6$, $R_{12}$, $R_{13}$, $R_{14}$ and X corresponds each to one row in table B.

TABLE 30

Compounds represented by the Formula I.30

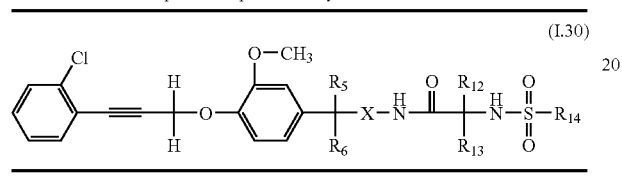

(I.30)

wherein the combination of the groups $R_5$, $R_6$, $R_{12}$, $R_{13}$, $R_{14}$ and X corresponds each to one row in table B.

TABLE B (Ph stands for phenyl):

| No. | $R_5$ | $R_6$ | X | $R_{12}$ | $R_{13}$ | $R_{14}$ |
|---|---|---|---|---|---|---|
| 001 | H | H | O | $CH_3$ | H | $CH_3$ |
| 002 | H | H | O | $CH_3$ | H | $CH_2CH_3$ |
| 003 | H | H | O | $CH_3$ | H | $N(CH_3)_2$ |
| 004 | $CH_3$ | H | O | $CH_3$ | H | $CH_3$ |
| 005 | $CH_3$ | H | O | $CH_3$ | H | $CH_2CH_3$ |
| 006 | $CH_3$ | H | O | $CH_3$ | H | $N(CH_3)_2$ |
| 007 | H | H | NH | $CH_3$ | H | $CH_3$ |
| 008 | H | H | NH | $CH_3$ | H | $CH_2CH_3$ |
| 009 | H | H | NH | $CH_3$ | H | $N(CH_3)_2$ |
| 010 | $CH_3$ | H | NH | $CH_3$ | H | $CH_3$ |
| 011 | $CH_3$ | H | NH | $CH_3$ | H | $CH_2CH_3$ |
| 012 | $CH_3$ | H | NH | $CH_3$ | H | $N(CH_3)_2$ |
| 013 | H | H | $NCH_3$ | $CH_3$ | H | $CH_3$ |
| 014 | H | H | $NCH_3$ | $CH_3$ | H | $CH_2CH_3$ |
| 015 | H | H | $NCH_3$ | $CH_3$ | H | $N(CH_3)_2$ |
| 016 | $CH_3$ | H | $NCH_3$ | $CH_3$ | H | $CH_3$ |
| 017 | $CH_3$ | H | $NCH_3$ | $CH_3$ | H | $CH_2CH_3$ |
| 018 | $CH_3$ | H | $NCH_3$ | $CH_3$ | H | $N(CH_3)_2$ |
| 019 | H | H | O | $CH_2CH_3$ | H | $CH_3$ |
| 020 | H | H | O | $CH_2CH_3$ | H | $CH_2CH_3$ |
| 021 | H | H | O | $CH2CH_3$ | H | $N(CH_3)_2$ |
| 022 | $CH_3$ | H | O | $CH_2CH_3$ | H | $CH_3$ |
| 023 | $CH_3$ | H | O | $CH_2CH_3$ | H | $CH_2CH_3$ |
| 024 | $CH_3$ | H | O | $CH_2CH_3$ | H | $N(CH_3)_2$ |
| 025 | H | H | NH | $CH_2CH_3$ | H | $CH_3$ |
| 026 | H | H | NH | $CH_2CH_3$ | H | $CH_2CH_3$ |
| 027 | H | H | NH | $CH_2CH_3$ | H | $N(CH_3)_2$ |
| 028 | $CH_3$ | H | NH | $CH_2CH_3$ | H | $CH_3$ |
| 029 | $CH_3$ | H | NH | $CH_2CH_3$ | H | $CH_2CH_3$ |
| 030 | $CH_3$ | H | NH | $CH_2CH_3$ | H | $N(CH_3)_2$ |
| 031 | H | H | $NCH_3$ | $CH_2CH_3$ | H | $CH_3$ |
| 032 | H | H | $NCH_3$ | $CH_2CH_3$ | H | $CH_2CH_3$ |
| 033 | H | H | $NCH_3$ | $CH_2CH_3$ | H | $N(CH_3)_2$ |
| 034 | $CH_3$ | H | $NCH_3$ | $CH_2CH_3$ | H | $CH_3$ |
| 035 | $CH_3$ | H | $NCH_3$ | $CH_2CH_3$ | H | $CH_2CH_3$ |
| 036 | $CH_3$ | H | $NCH_3$ | $CH_2CH_3$ | H | $N(CH_3)_2$ |
| 037 | H | H | O | $CH_2CH_2CH_3$ | H | $CH_3$ |
| 038 | H | H | O | $CH_2CH_2CH_3$ | H | $CH_2CH_3$ |
| 039 | H | H | O | $CH_2CH_2CH_3$ | H | $N(CH_3)_2$ |
| 040 | $CH_3$ | H | O | $CH_2CH_2CH_3$ | H | $CH_3$ |
| 041 | $CH_3$ | H | O | $CH_2CH_2CH_3$ | H | $CH_2CH_3$ |
| 042 | $CH_3$ | H | O | $CH_2CH_2CH_3$ | H | $N(CH_3)_2$ |
| 043 | H | H | NH | $CH_2CH_2CH_3$ | H | $CH_3$ |
| 044 | H | H | NH | $CH_2CH_2CH_3$ | H | $CH_2CH_3$ |
| 045 | H | H | NH | $CH_2CH_2CH_3$ | H | $N(CH_3)_2$ |
| 046 | $CH_3$ | H | NH | $CH_2CH_2CH_3$ | H | $CH_3$ |
| 047 | $CH_3$ | H | NH | $CH_2CH_2CH_3$ | H | $CH_2CH_3$ |
| 048 | $CH_3$ | H | NH | $CH_2CH_2CH_3$ | H | $N(CH_3)_2$ |
| 049 | H | H | $NCH_3$ | $CH_2CH_2CH_3$ | H | $CH_3$ |
| 050 | H | H | $NCH_3$ | $CH_2CH_2CH_3$ | H | $CH_2CH_3$ |
| 051 | H | H | $NCH_3$ | $CH_2CH_2CH_3$ | H | $N(CH_3)_2$ |
| 052 | $CH_3$ | H | $NCH_3$ | $CH_2CH_2CH_3$ | H | $CH_3$ |
| 053 | $CH_3$ | H | $NCH_3$ | $CH_2CH_2CH_3$ | H | $CH_2CH_3$ |
| 054 | $CH_3$ | H | $NCH_3$ | $CH_2CH_2CH_3$ | H | $N(CH_3)_2$ |
| 055 | H | H | O | $CH(CH_3)_2$ | H | $CH_3$ |
| 056 | H | H | O | $CH(CH_3)_2$ | H | $CH_2CH_3$ |
| 057 | H | H | O | $CH(CH_3)_2$ | H | $N(CH_3)_2$ |
| 058 | $CH_3$ | H | O | $CH(CH_3)_2$ | H | $CH_3$ |
| 059 | $CH_3$ | H | O | $CH(CH_3)_2$ | H | $CH_2CH_3$ |
| 060 | $CH_3$ | H | O | $CH(CH_3)_2$ | H | $N(CH_3)_2$ |
| 061 | H | H | NH | $CH(CH_3)_2$ | H | $CH_3$ |
| 062 | H | H | NH | $CH(CH_3)_2$ | H | $CH_2CH_3$ |
| 063 | H | H | NH | $CH(CH_3)_2$ | H | $N(CH_3)_2$ |
| 064 | $CH_3$ | H | NH | $CH(CH_3)_2$ | H | $CH_3$ |
| 065 | $CH_3$ | H | NH | $CH(CH_3)_2$ | H | $CH_2CH_3$ |
| 066 | $CH_3$ | H | NH | $CH(CH_3)_2$ | H | $N(CH_3)_2$ |
| 067 | H | H | $NCH_3$ | $CH(CH_3)_2$ | H | $CH_3$ |
| 068 | H | H | $NCH_3$ | $CH(CH_3)_2$ | H | $CH_2CH_3$ |
| 069 | H | H | $NCH_3$ | $CH(CH_3)_2$ | H | $N(CH_3)_2$ |
| 070 | $CH_3$ | H | $NCH_3$ | $CH(CH_3)_2$ | H | $CH_3$ |
| 071 | $CH_3$ | H | $NCH_3$ | $CH(CH_3)_2$ | H | $CH_2CH_3$ |
| 072 | $CH_3$ | H | $NCH_3$ | $CH(CH_3)_2$ | H | $N(CH_3)_2$ |
| 073 | H | H | O | $C_3H_5$-cycl | H | $CH_3$ |
| 074 | H | H | O | $C_3H_5$-cycl | H | $CH_2CH_3$ |
| 075 | H | H | O | $C_3H_5$-cycl | H | $N(CH_3)_2$ |
| 076 | $CH_3$ | H | O | $C_3H_5$-cycl | H | $CH_3$ |
| 077 | $CH_3$ | H | O | $C_3H_5$-cycl | H | $CH_2CH_3$ |
| 078 | $CH_3$ | H | O | $C_3H_5$-cycl | H | $N(CH_3)_2$ |
| 079 | H | H | NH | $C_3H_5$-cycl | H | $CH_3$ |
| 080 | H | H | NH | $C_3H_5$-cycl | H | $CH_2CH_3$ |
| 081 | H | H | NH | $C_3H_5$-cycl | H | $N(CH_3)_2$ |
| 082 | $CH_3$ | H | NH | $C_3H_5$-cycl | H | $CH_3$ |
| 083 | $CH_3$ | H | NH | $C_3H_5$-cycl | H | $CH_2CH_3$ |
| 084 | $CH_3$ | H | NH | $C_3H_5$-cycl | H | $N(CH_3)_2$ |
| 085 | H | H | $NCH_3$ | $C_3H_5$-cycl | H | $CH_3$ |
| 086 | H | H | $NCH_3$ | $C_3H_5$-cycl | H | $CH_2CH_3$ |
| 087 | H | H | $NCH_3$ | $C_3H_5$-cycl | H | $N(CH_3)_2$ |
| 088 | $CH_3$ | H | $NCH_3$ | $C_3H_5$-cycl | H | $CH_3$ |
| 089 | $CH_3$ | H | $NCH_3$ | $C_3H_5$-cycl | H | $CH_2CH_3$ |
| 090 | $CH_3$ | H | $NCH_3$ | $C_3H_5$-cycl | H | $N(CH_3)_2$ |
| 091 | H | H | O | $CHCH_3(CH_2CH_3)$ | H | $CH_3$ |
| 092 | H | H | O | $CHCH_3(CH_2CH_3)$ | H | $CH_2CH_3$ |
| 093 | H | H | O | $CHCH_3(CH_2CH_3)$ | H | $N(CH_3)_2$ |
| 094 | $CH_3$ | H | O | $CHCH_3(CH_2CH_3)$ | H | $CH_3$ |
| 095 | $CH_3$ | H | O | $CHCH_3(CH_2CH_3)$ | H | $CH_2CH_3$ |
| 096 | $CH_3$ | H | O | $CHCH_3(CH_2CH_3)$ | H | $N(CH_3)_2$ |
| 097 | H | H | NH | $CHCH_3(CH_2CH_3)$ | H | $CH_3$ |
| 098 | H | H | NH | $CHCH_3(CH_2CH_3)$ | H | $CH_2CH_3$ |
| 099 | H | H | NH | $CHCH_3(CH_2CH_3)$ | H | $N(CH_3)_2$ |
| 100 | $CH_3$ | H | NH | $CHCH_3(CH_2CH_3)$ | H | $CH_3$ |
| 101 | $CH_3$ | H | NH | $CHCH_3(CH_2CH_3)$ | H | $CH_2CH_3$ |
| 102 | $CH_3$ | H | NH | $CHCH_3(CH_2CH_3)$ | H | $N(CH_3)_2$ |
| 103 | H | H | $NCH_3$ | $CHCH_3(CH_2CH_3)$ | H | $CH_3$ |
| 104 | H | H | $NCH_3$ | $CHCH_3(CH_2CH_3)$ | H | $CH_2CH_3$ |
| 105 | H | H | $NCH_3$ | $CHCH_3(CH_2CH_3)$ | H | $N(CH_3)_2$ |
| 106 | $CH_3$ | H | $NCH_3$ | $CHCH_3(CH_2CH_3)$ | H | $CH_3$ |
| 107 | $CH_3$ | H | $NCH_3$ | $CHCH_3(CH_2CH_3)$ | H | $CH_2CH_3$ |
| 108 | $CH_3$ | H | $NCH_3$ | $CHCH_3(CH_2CH_3)$ | H | $N(CH_3)_2$ |
| 109 | H | H | O | Ph | H | $CH_3$ |
| 110 | H | H | O | Ph | H | $CH_2CH_3$ |
| 111 | H | H | O | Ph | H | $N(CH_3)_2$ |
| 112 | $CH_3$ | H | O | Ph | H | $CH_3$ |
| 113 | $CH_3$ | H | O | Ph | H | $CH_2CH_3$ |
| 114 | $CH_3$ | H | O | Ph | H | $N(CH_3)_2$ |
| 115 | H | H | NH | Ph | H | $CH_3$ |
| 116 | H | H | NH | Ph | H | $CH_2CH_3$ |

TABLE B-continued (Ph stands for phenyl):

| No. | R5 | R6 | X | R12 | R13 | R14 |
|---|---|---|---|---|---|---|
| 117 | H | H | NH | Ph | H | CH3 |
| 118 | CH3 | H | NH | Ph | H | CH3 |
| 119 | CH3 | H | NH | Ph | H | CH2CH3 |
| 120 | CH3 | H | NH | Ph | H | N(CH3)2 |
| 121 | H | H | NCH3 | Ph | H | CH3 |
| 122 | H | H | NCH3 | Ph | H | CH2CH3 |
| 123 | H | H | NCH3 | Ph | H | N(CH3)2 |
| 124 | CH3 | H | NCH3 | Ph | H | CH3 |
| 125 | CH3 | H | NCH3 | Ph | H | CH2CH3 |
| 126 | CH3 | H | NCH3 | Ph | H | N(CH3)2 |
| 127 | H | H | O | 4-CH3—Ph | H | CH3 |
| 128 | H | H | O | 4-CH3—Ph | H | CH2CH3 |
| 129 | H | H | O | 4-CH3—Ph | H | N(CH3)2 |
| 130 | CH3 | H | O | 4-CH3—Ph | H | CH3 |
| 131 | CH3 | H | O | 4-CH3—Ph | H | CH2CH3 |
| 132 | CH3 | H | O | 4-CH3—Ph | H | N(CH3)2 |
| 133 | H | H | NH | 4-CH3—Ph | H | CH3 |
| 134 | H | H | NH | 4-CH3—Ph | H | CH2CH3 |
| 135 | H | H | NH | 4-CH3—Ph | H | N(CH3)2 |
| 136 | CH3 | H | NH | 4-CH3—Ph | H | CH3 |
| 137 | CH3 | H | NH | 4-CH3—Ph | H | CH2CH3 |
| 138 | CH3 | H | NH | 4-CH3—Ph | H | N(CH3)2 |
| 139 | H | H | NCH3 | 4-CH3—Ph | H | CH3 |
| 140 | H | H | NCH3 | 4-CH3—Ph | H | CH2CH3 |
| 141 | H | H | NCH3 | 4-CH3—Ph | H | N(CH3)2 |
| 142 | CH3 | H | NCH3 | 4-CH3—Ph | H | CH3 |
| 143 | CH3 | H | NCH3 | 4-CH3—Ph | H | CH2CH3 |
| 144 | CH3 | H | NCH3 | 4-CH3—Ph | H | N(CH3)2 |
| 145 | H | H | O | 4-Br—Ph | H | CH3 |
| 146 | H | H | O | 4-Br—Ph | H | CH2CH3 |
| 147 | H | H | O | 4-Br—Ph | H | N(CH3)2 |
| 148 | CH3 | H | O | 4-Br—Ph | H | CH3 |
| 149 | CH3 | H | O | 4-Br—Ph | H | CH2CH3 |
| 150 | CH3 | H | O | 4-Br—Ph | H | N(CH3)2 |
| 151 | H | H | NH | 4-Br—Ph | H | CH3 |
| 152 | H | H | NH | 4-Br—Ph | H | CH2CH3 |
| 153 | H | H | NH | 4-Br—Ph | H | N(CH3)2 |
| 154 | CH3 | H | NH | 4-Br—Ph | H | CH3 |
| 155 | CH3 | H | NH | 4-Br—Ph | H | CH2CH3 |
| 156 | CH3 | H | NH | 4-Br—Ph | H | N(CH3)2 |
| 157 | H | H | NCH3 | 4-Br—Ph | H | CH3 |
| 158 | H | H | NCH3 | 4-Br—Ph | H | CH2CH3 |
| 159 | H | H | NCH3 | 4-Br—Ph | H | N(CH3)2 |
| 160 | CH3 | H | NCH3 | 4-Br—Ph | H | CH3 |
| 161 | CH3 | H | NCH3 | 4-Br—Ph | H | CH2CH3 |
| 162 | CH3 | H | NCH3 | 4-Br—Ph | H | N(CH3)2 |
| 163 | H | H | O | 4-Cl—Ph | H | CH3 |
| 164 | H | H | O | 4-Cl—Ph | H | CH2CH3 |
| 165 | H | H | O | 4-Cl—Ph | H | N(CH3)2 |
| 166 | CH3 | H | O | 4-Cl—Ph | H | CH3 |
| 167 | CH3 | H | O | 4-Cl—Ph | H | CH2CH3 |
| 168 | CH3 | H | O | 4-Cl—Ph | H | N(CH3)2 |
| 169 | H | H | NH | 4-Cl—Ph | H | CH3 |
| 170 | H | H | NH | 4-Cl—Ph | H | CH2CH3 |
| 171 | H | H | NH | 4-Cl—Ph | H | N(CH3)2 |
| 172 | CH3 | H | NH | 4-Cl—Ph | H | CH3 |
| 173 | CH3 | H | NH | 4-Cl—Ph | H | CH2CH3 |
| 174 | CH3 | H | NH | 4-Cl—Ph | H | N(CH3)2 |
| 175 | H | H | NCH3 | 4-Cl—Ph | H | CH3 |
| 176 | H | H | NCH3 | 4-Cl—Ph | H | CH2CH3 |
| 177 | H | H | NCH3 | 4-Cl—Ph | H | N(CH3)2 |
| 178 | CH3 | H | NCH3 | 4-Cl—Ph | H | CH3 |
| 179 | CH3 | H | NCH3 | 4-Cl—Ph | H | CH2CH3 |
| 180 | CH3 | H | NCH3 | 4-Cl—Ph | H | N(CH3)2 |
| 181 | H | H | O | 3,4-Cl2—Ph | H | CH3 |
| 182 | H | H | O | 3,4-Cl2—Ph | H | CH2CH3 |
| 183 | H | H | O | 3,4-Cl2—Ph | H | N(CH3)2 |
| 184 | CH3 | H | O | 3,4-Cl2—Ph | H | CH3 |
| 185 | CH3 | H | O | 3,4-Cl2—Ph | H | CH2CH3 |
| 186 | CH3 | H | O | 3,4-Cl2—Ph | H | N(CH3)2 |
| 187 | H | H | NH | 3,4-Cl2—Ph | H | CH3 |
| 188 | H | H | NH | 3,4-Cl2—Ph | H | CH2CH3 |
| 189 | H | H | NH | 3,4-Cl2—Ph | H | N(CH3)2 |
| 190 | CH3 | H | NH | 3,4-Cl2—Ph | H | CH3 |
| 191 | CH3 | H | NH | 3,4-Cl2—Ph | H | CH2CH3 |
| 192 | CH3 | H | NH | 3,4-Cl2—Ph | H | N(CH3)2 |
| 193 | H | H | NCH3 | 3,4-Cl2—Ph | H | CH3 |
| 194 | H | H | NCH3 | 3,4-Cl2—Ph | H | CH2CH3 |
| 195 | H | H | NCH3 | 3,4-Cl2—Ph | H | N(CH3)2 |
| 196 | CH3 | H | NCH3 | 3,4-Cl2—Ph | H | CH3 |
| 197 | CH3 | H | NCH3 | 3,4-Cl2—Ph | H | CH2CH3 |
| 198 | CH3 | H | NCH3 | 3,4-Cl2—Ph | H | N(CH3)2 |
| 199 | H | H | O | 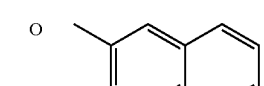 | H | CH3 |
| 200 | H | H | O | 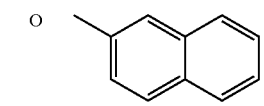 | H | CH2CH3 |
| 201 | H | H | O | 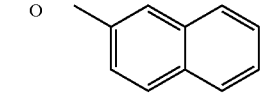 | H | N(CH3)2 |
| 202 | CH3 | H | O | 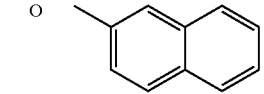 | H | CH3 |
| 203 | CH3 | H | O | 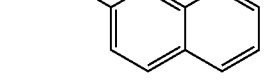 | H | CH2CH3 |
| 204 | CH3 | H | O | 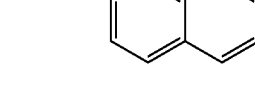 | H | N(CH3)2 |
| 205 | H | H | NH | 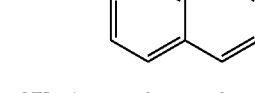 | H | CH3 |
| 206 | H | H | NH | 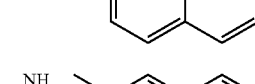 | H | CH2CH3 |
| 207 | H | H | NH | 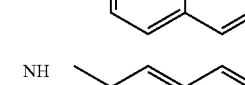 | H | N(CH3)2 |
| 208 | CH3 | H | NH | 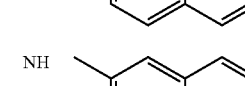 | H | CH3 |
| 209 | CH3 | H | NH | 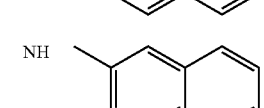 | H | CH2CH3 |
| 210 | CH3 | H | NH |  | H | N(CH3)2 |

TABLE B-continued (Ph stands for phenyl):

| No. | R$_5$ | R$_6$ | X | R$_{12}$ | R$_{13}$ | R$_{14}$ |
|---|---|---|---|---|---|---|
| 211 | H | H | NCH$_3$ | 2-naphthyl | H | CH$_3$ |
| 212 | H | H | NCH$_3$ | 2-naphthyl | H | CH$_2$CH$_3$ |
| 213 | H | H | NCH$_3$ | 2-naphthyl | H | N(CH$_3$)$_2$ |
| 214 | CH$_3$ | H | NCH$_3$ | 2-naphthyl | H | CH$_3$ |
| 215 | CH$_3$ | H | NCH$_3$ | 2-naphthyl | H | CH$_2$CH$_3$ |
| 216 | CH$_3$ | H | NCH$_3$ | 2-naphthyl | H | N(CH$_3$)$_2$ |

Formulations may be prepared analogously to those described in, for example, WO 95/30651, which is incorporated by reference in its entirety for all useful purposes.

Biological Examples

D-1: Action against *Plasmopara viticola* (Downy Mildew) on Vines 5 week old grape seedlings cv. Gutedel are treated with the formulated test compound in a spray chamber. One day after application grape plants are inoculated by spraying a sporangia suspension ($4 \times 10^4$ sporangia/ml) on the lower leaf side of the test plants. After an incubation period of 6 days at +21° C. and 95% r.h. in a greenhouse the disease incidence is assessed.

Compounds of Tables 1 to 30 exhibit a good fungicidal action against *Plasmopara viticola* on vines. Compounds 1.004, 1.040, 5.004, 5.037, 5.040, 5.091, 23.055 and 23.056 at 200 ppm inhibit fungal infestation in this test to at least 80%, while under the same conditions untreated control plants are infected by the phytopathogenic fungi to over 80%.

D-2: Action against *Phytophthora* (Late Blight) on Tomato Plants 3 week old tomato plants cv. Roter Gnom are treated with the formulated test compound in a spray chamber. Two day after application the plants are inoculated by spraying a sporangia suspension ($2 \times 10^4$ sporangia/ml) on the test plants. After an incubation period of 4 days at +18° C. and 95% r.h. in a growth chamber the disease incidence is assessed. Compounds of Tables 1 to 30 exhibit a long-lasting effect against fungus infestation. Compounds 1.004, 1.040, 1.055, 1.091, 5.004, 5.037, 5.040, 5.055, 5.091, 5.163, 23.055, 23.056 and 23.057 at 200 ppm inhibit fungal infestation in this test to at least 80%, while under the same conditions untreated control plants are infected by the phytopathogenic fungi to over 80%.

D-3: Action against *Phytophthora* (Late Blight) on Potato Plants 5 week old potato plants cv. Bintje are treated with the formulated test compound in a spray chamber. Two day after application the plants are inoculated by spraying a sporangia suspension ($14 \times 10^4$ sporangia/ml) on the test plants. After an incubation period of 4 days at +18° C. and 95% r.h. in a growth chamber the disease incidence is assessed. Fungal infestation is effectively controlled with compounds of Tables 1 to 30. Compounds 1.040, 5.004, 5.040 and 23.055 at 200 ppm inhibit fungal infestation in this test to at least 80%, while under the same conditions untreated control plants are infected by the phytopathogenic fungi to over 80%.

What is claimed is:

1. A compound of formula I

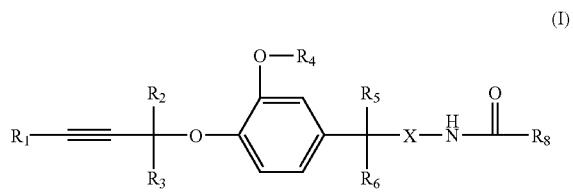

(I)

including the optical isomers thereof and mixtures of such isomers, wherein

R$_1$ is hydrogen, C$_1$–C$_8$-alkyl, C$_3$–C$_8$-cycloalkyl, phenyl or naphthyl; phenyl and naphthyl being optionally substituted by one to three substituents selected from the group comprising C$_1$–C$_8$-alkyl, C$_2$–C$_8$-alkenyl, C$_2$–C$_8$-alkynyl, C$_1$–C$_8$-haloalkyl, C$_1$–C$_8$-alkoxy, C$_1$–C$_8$-haloalkoxy, C$_1$–C$_8$-alkylthio, C$_1$–C$_8$-haloalkylthio, C$_1$–C$_8$-alkylsulfonyl, halogen, cyano and nitro;

R$_2$, R$_3$, R$_5$, R$_6$, and R$_7$ are each independently of each other hydrogen or C$_1$–C$_6$-alkyl;

R$_4$ is C$_1$–C$_6$-alkyl; or

X is O or N—R$_7$; and

R$_8$ is a group

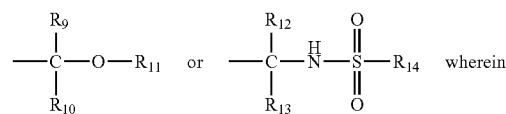

wherein

R$_9$ is phenyl, naphthyl, 1,3-biphenyl or 1,4-biphenyl, each optionally substituted by one to three substituents selected from the group comprising C$_1$–C$_8$-alkyl, C$_2$–C$_8$-alkenyl, C$_2$–C$_8$-alkynyl, C$_1$–C$_8$-haloalkyl, C$_1$–C$_8$-alkoxy, C$_1$–C$_8$-haloalkoxy, C$_1$–C$_8$-alkylthio, C$_1$–C$_8$-haloalkylthio, C$_1$–C$_8$-alkylsulfonyl, halogen, cyano, nitro and C$_1$–C$_8$-alkoxycarbonyl;

R$_{10}$ and R$_{11}$ are each independently hydrogen, C$_1$–C$_8$-alkyl, C$_1$–C$_8$-haloalkyl, C$_3$–C$_8$-alkenyl or C$_3$–C$_8$-alkynyl;

R$_{12}$ is C$_1$–C$_8$-alkyl, C$_3$–C$_8$-cycloalkyl, phenyl or naphthyl; phenyl and naphthyl being optionally substituted by one to three substituents selected from the group comprising C$_1$–C$_8$-alkyl, C$_2$–C$_8$-alkenyl, C$_2$–C$_8$-alkynyl, C$_1$–C$_8$-haloalkyl, C$_1$–C$_8$-alkoxy, C$_1$–C$_8$-haloalkoxy, C$_1$–C$_8$-alkylthio, C$_1$–C$_8$-haloalkylthio, $C_1$–$C_8$-alkylsulfonyl, aryl, halogen, cyano and nitro $R_{13}$ is hydrogen, $C_1$–$C_8$-alkyl, $C_1$–$C_8$-haloalkyl, $C_3$–$C_8$-alkenyl or $C_3$–$C_8$-alkynyl; and $R_{14}$ is $C_1$–$C_8$-alkyl, $C_1$–$C_8$-haloalkyl, $C_1$–$C_8$-alkylamino or $C_1$–$C_8$-dialkylamino.

2. A compound according to claim 1 wherein $R_{10}$ is hydrogen or $C_1$–$C_8$-alkyl, X is oxygen, $R_8$ is —C($R_9R_{10}$)—$OR_{11}$ and $R_{11}$, is hydrogen or $C_3$–$C_8$-alkynyl.

3. A compound according to claim 1 wherein X is oxygen, $R_8$ is —C($R_{12}R_{13}$)NH—$SO_2$—$R_{14}$, and $R_{12}$ is $C_1$–$C_8$-alkyl or branched $C_1$–$C_8$-alkyl.

4. A compound of formula I according to claim 1, wherein $R_1$ is hydrogen, $C_1$–$C_8$-alkyl, $C_3$–$C_8$-cycloalkyl, phenyl or naphthyl; phenyl and naphthyl being optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano and nitro;

$R_4$ is $C_1$–$C_6$-alkyl; or
$R_8$ is a group

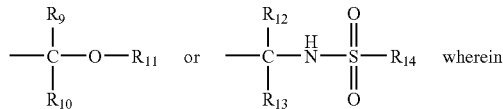

$R_9$ is phenyl, naphthyl, 1,3-biphenyl or 1,4-biphenyl, each optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl;

$R_{11}$, is hydrogen, $C_1$–$C_8$-alkyl or $C_3$–$C_8$-alkynyl; and
$R_{14}$ is $C_1$–$C_8$-alkyl, $C_1$–$C_8$-haloalkyl, $C_1$–$C_8$-alkylamino or $C_1$–$C_8$-dialkylamino.

5. A compound of formula I according to claim 1, wherein $R_1$ is hydrogen, $C_1$–$C_8$-alkyl, $C_3$–$C_8$-cycloalkyl; and $R_2$, $R_3$, $R_5$ and $R_6$ are hydrogen; and $R_4$ is $C_1$–$C_6$-alkyl; and $R_9$ is phenyl, naphthyl, 1,3-biphenyl or 1,4-biphenyl, each optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; and $R_{10}$ is hydrogen or $C_1$–$C_4$-alkyl; and $R_{11}$ is hydrogen, $C_1$–$C_8$-alkyl or $C_2$–$C_8$-alkynyl; and $R_{12}$ is $C_1$–$C_8$-alkyl, $C_3$–$C_6$-cycloalkyl, $C_3$–$C_8$-alkenyl, $C_3$–$C_8$-alkynyl; phenyl or benzyl wherein the phenyl and benzyl is optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; and $R_{13}$ is hydrogen or $C_1$–$C_4$-alkyl; and $R_{14}$ is $C_1$–$C_6$-alkyl; $C_1$–$C_6$-monoalkylamino or $C_1$–$C_6$-dialkylamino.

6. A compound of formula I according to claim 1, wherein $R_1$ is hydrogen or $C_1$–$C_6$-alkyl, and $R_2$, $R_3$, $R_5$ and $R_6$ are hydrogen; and $R_4$ is methyl or ethyl; and $R_9$ is phenyl or naphthyl each optionally substituted by one to three substituents selected from the group comprising $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, cyano, nitro and $C_1$–$C_6$-alkoxycarbonyl; and $R_{10}$ and $R_{13}$ are each hydrogen; and $R_{11}$ is hydrogen or $C_2$–$C_6$-alkynyl; and $R_{12}$ is $C_2$–$C_6$-alkyl or $C_3$–$C_6$-cycloalkyl; and $R_{14}$ is $C_1$–$C_6$-alkyl or $C_1$–$C_6$-dialkylamino.

7. A compound of formula I according to claim 1 selected from the group comprising 2-hydroxy-N-(3-methoxy-4-prop-2-ynyloxy-benzyloxy)-2-phenyl-acetamide, N-(3-methoxy-4-prop-2-ynyloxy-benzyloxy)-2-phenyl-2-prop-2-ynyloxy-acetamide, 2-hydroxy-N-(3-methoxy-4-pent-2-ynyloxy-benzyloxy)-2-phenyl-acetamide, N-(3-methoxy-4-pent-2-ynyloxy-benzyloxy)-2-phenyl-2-prop-2-ynyloxy-acetamide, 2-(4-chloro-phenyl)-2-hydroxy-N-(3-methoxy-4-prop-2-ynyloxy-benzyloxy)-acetamide, 2-(4-chloro-phenyl)-N-(3-methoxy-4-prop-2-ynyloxy-benzyloxy)-2-prop-2-ynyloxy-acetamide, 2-(4-chloro-phenyl)-2-hydroxy-N-(3-methoxy-4-pent-2-ynyloxy-benzyloxy)-acetamide, 2-(4-chloro-phenyl)-N-(3-methoxy-4-pent-2-ynyloxy-benzyloxy)-2-prop-2-ynyloxy-acetamide, 2-(4-bromo-phenyl)-2-hydroxy-N-(3-methoxy-4-prop-2-ynyloxy-benzyloxy)-acetamide, 2-(4-bromo-phenyl)-N-(3-methoxy-4-prop-2-ynyloxy-benzyloxy)-2-prop-2-ynyloxy-acetamide, 2-(4-bromo-phenyl)-2-hydroxy-N-(3-methoxy-4-pent-2-ynyloxy-benzyloxy)-acetamide, 2-(4-bromo-phenyl)-N-(3-methoxy-4-pent-2-ynyloxy-benzyloxy)-2-prop-2-ynyloxy-acetamide, 2-(3,4-dichloro-phenyl)-2-hydroxy-N-(3-methoxy-4-prop-2-ynyloxy-benzyloxy)-acetamide, 2-(3,4-dichloro-phenyl)-N-(3-methoxy-4-prop-2-ynyloxy-benzyloxy)-2-prop-2-ynyloxy-acetamide, 2-(3,4-dichloro-phenyl)-2-hydroxy-N-(3-methoxy-4-pent-2-ynyloxy-benzyloxy)-acetamide, 2-(3,4-dichloro-phenyl)-N-(3-methoxy-4-pent-2-ynyloxy-benzyloxy)-2-prop-2-ynyloxy-acetamide, (S)-2-methylsulfonylamino-N-(3-methoxy-4-prop-2-ynyloxy-benzyloxy)-3-methyl-butyramide, (S)-2-methylsulfonylamino-N-(3-methoxy-4-pent-2-ynyloxy-benzyloxy)-3-methyl-butyramide, (S)-N-{4-[3-(4-chloro-phenyl)-prop-2-ynyloxy]-3-methoxy-benzyloxy}-2-methylsulfonylamino-3-methyl-butyramide, (S)-2-ethylsulfonylamino-N-(3-methoxy-4-prop-2-ynyloxy-benzyloxy)-3-methyl-butyramide, (S)-N-{4-[3-(4-chloro-phenyl)-prop-2-ynyloxy]-3-methoxy-benzyloxy}-2-N,N'-dimethylamino-sulfonylamino-3-methyl-butyramide, 2-(4-ethyl-phenyl)-2-hydroxy-N-(3-methoxy-4-prop-2-ynyloxy-benzyloxy)-acetamide, 2-(4-ethyl-phenyl)-2-hydroxy-N-(3-methoxy-4-pent-2-ynyloxy-benzyloxy)-acetamide, (S)-2-ethylsulfonylamino-N-(3-methoxy-4-pent-2-ynyloxy-benzyloxy)-3-methyl-butyramide, (S)-N-{4-[3-(4-chloro-phenyl)-prop-2-ynyloxy]-3-methoxy-benzyloxy}-2-ethanesulfonylamino-3-methyl-butyramide, hydroxy-phenyl-acetic acid N'-(3-methoxy-4-prop-2-ynyloxy-benzyl)-hydrazide, phenyl-prop-2-ynyloxy-acetic acid N'-(3-methoxy-4-prop-2-ynyloxy-benzyl)-hydrazide, hydroxy-phenyl-acetic acid N'-(3-methoxy-4-pent-2-ynyloxy-benzyl)-hydrazide, phenyl-prop-2-ynyloxy-acetic acid N'-(3-methoxy-4-pent-2-ynyloxy-benzyl)-hydrazide,
(4-chloro-phenyl)-hydroxy-acetic acid N'-(3-methoxy-4-prop-2-ynyloxy-benzyl)-hydrazide,
(4-chloro-phenyl)-prop-2-ynyloxy-acetic acid N'-(3-methoxy-4-prop-2-ynyloxy-benzyl)-hydrazide,
(4-chloro-phenyl)-hydroxy-acetic acid N'-(3-methoxy-4-pent-2-ynyloxy-benzyl)-hydrazide,
(4-chloro-phenyl)-prop-2-ynyloxy-acetic acid N'-(3-methoxy-4-pent-2-ynyloxy-benzyl)-hydrazide,
(4-bromo-phenyl)-hydroxy-acetic acid N'-(3-methoxy-4-prop-2-ynyloxy-benzyl)-hydrazide,
(4-bromo-phenyl)-prop-2-ynyloxy-acetic acid N'-(3-methoxy-4-prop-2-ynyloxy-benzyl)-hydrazide,
(4-bromo-phenyl)-hydroxy-acetic acid N'-(3-methoxy-4-pent-2-ynyloxy-benzyl)-hydrazide,
(4-bromo-phenyl)-prop-2-ynyloxy-acetic acid N'-(3-methoxy-4-pent-2-ynyloxy-benzyl)-hydrazide,
(3,4-dichloro-phenyl)-hydroxy-acetic acid N'-(3-methoxy-4-prop-2-ynyloxy-benzyl)-hydrazide,
(3,4-dichloro-phenyl)-prop-2-ynyloxy-acetic acid N'-(3-methoxy-4-prop-2-ynyloxy-benzyl)-hydrazide,
(3,4-dichloro-phenyl)-hydroxy-acetic acid N'-(3-methoxy-4-pent-2-ynyloxy-benzyl)-hydrazide,
(3,4-dichloro-phenyl)-prop-2-ynyloxy-acetic acid N'-(3-methoxy-4-pent-2-ynyloxy-benzyl)-hydrazide,
N-{(S)-1-[N'-(3-methoxy-4-prop-2-ynyloxy-benzyl)-hydrazinocarbonyl]-2-methyl-propyl}-methylsulfonamide,
N-{(S)-1-[N'-(3-methoxy-4-pent-2-ynyloxy-benzyl)-hydrazinocarbonyl]-2-methyl-propyl}-methylsulfonamide,
N-[(S)-1-(N'-{4-[3-(4-chloro-phenyl)-prop-2-ynyloxy]-3-methoxy-benzyl}-hydrazinocarbonyl)-2-methyl-propyl]-methylsulfonamide,
N-{(S)-1-[N'-(3-methoxy-4-prop-2-ynyloxy-benzyl)-hydrazinocarbonyl]-2-methyl-propyl}-ethylsulfonamide,
N-{(S)-1-[N'-(3-methoxy-4-pent-2-ynyloxy-benzyl)-hydrazinocarbonyl]-2-methyl-propyl}-ethylsulfonamide, and
N-[(S)-1-(N'-{4-[3-(4-chloro-phenyl)-prop-2-ynyloxy]-3-methoxy-benzyl}-hydrazinocarbonyl)-2-methyl-propyl]-ethylsulfonamide.

8. A process for the preparation of a compound of formula I according to claim 1, which comprises a) reacting an acid of formula II or a carboxy-activated derivative of an acid of formula II

wherein $R_8$ is as defined for formula I with an amine of formula III

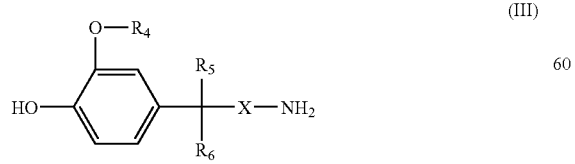

wherein $R_4$, $R_5$, $R_6$ and X are as defined for formula I and reacting the intermediate phenol of formula IV

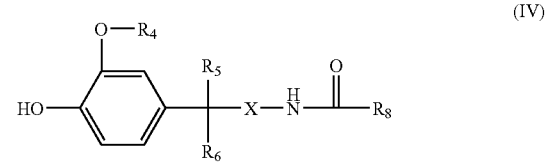

wherein $R_4$, $R_5$, $R_6$, $R_8$ and X are as defined for formula I with a compound of formula V

wherein $R_1$, $R_2$ and $R_3$ are as defined for formula I and wherein Y is a leaving group; or b) reacting a compound of formula VI

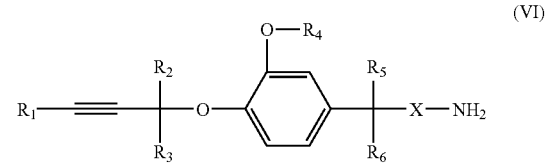

wherein $R_1$, $R_2$, $R_3$, $R_4$, $R_5$, $R_6$ and X are as defined for formula I with an acid of formula II or a carboxy-activated derivative of an acid of formula II; or c) reacting a compound of formula VIII

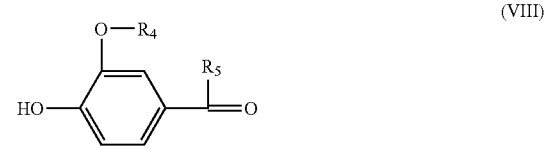

wherein $R_4$ and $R_5$ are as defined for formula I with an acid hydrazide of formula VII

wherein $R_8$ is as defined for formula I, and hydrating the intermediate acylhydrazone of formula IX

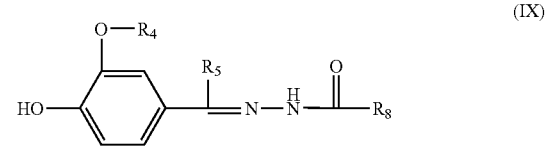

yielding in a compound of formula IVa, wherein $R_4$, $R_5$ and $R_8$ are as defined for formula I; or d) reacting a phenol of formula X

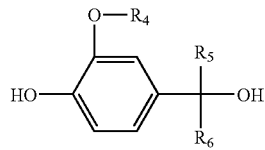
(X)

wherein $R_4$, $R_5$ and $R_6$ are as defined for formula I, with a compound of formula V as defined above, and transforming the intermediate alcohol of formula XI

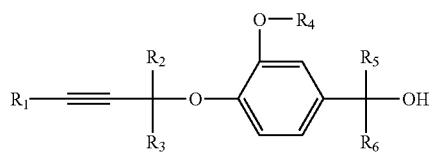
(XI)

wherein $R_1$, $R_2$, $R_3$, $R_4$, $R_5$ and $R_6$ are as defined for formula I, into a compound of formula XII,

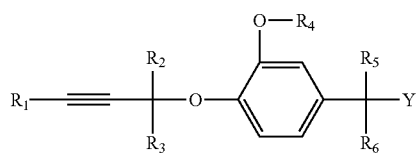
(XII)

wherein $R_1$, $R_2$, $R_3$, $R_4$, $R_5$ and $R_6$ are as defined for formula I and wherein Y is a leaving group like a halide such as a chloride or bromide or a sulfonic ester such as a tosylate, mesylate or triflate, and reacting the compound of formula XII with a compound of formula XIII

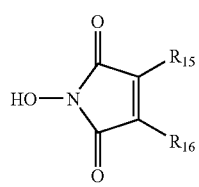
(XIII)

wherein $R_{15}$ and $R_{16}$ are hydrogen, halogen, methyl or part of an annelated benzene ring to yield an N-alkoxyimide of formula XIV

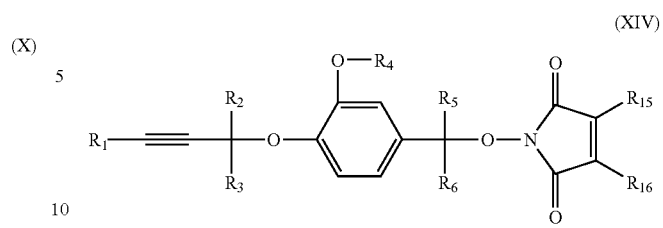
(XIV)

wherein $R_1$, $R_2$, $R_3$, $R_4$, $R_5$ and $R_6$ are as defined for formula I and $R_{15}$ and $R_{16}$ are as defined for formula XIII, and reacting the n-alkoxyimide of formula XIV with an amine derivative, like methylamine or butylamine or a hydrazine derivative, such as hydrazine, hydrazine hydrate or methylhydrazine to yield a compound of formula VIa

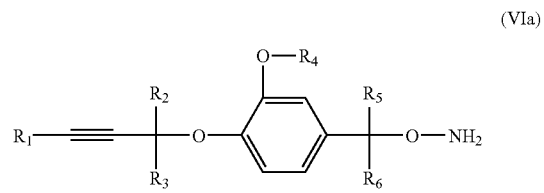
(VIa)

wherein $R_1$, $R_2$, $R_3$, $R_4$, $R_5$ and $R_6$ are as defined for formula I.

9. A composition for controlling and protecting against phytopathogenic microorganisms, comprising a compound of formula I according to claim 1 as active ingredient together with a suitable carrier.

10. A method of controlling and preventing an infestation of crop plants by phytopathogenic microorganisms, which comprises the application of a compound of formula I according to claim 1 as active ingredient to the plant, to parts of plants or to the locus thereof.

11. A method according to claim 10, wherein the phytopathogenic microorganisms are fungal organisms.

12. A method of controlling and preventing an infestation of crop plants by phytopathogenic microorganisms, which comprises the application of a composition according to claim 9 to plant, to parts of plants or to the locus thereof.

13. A method according to claim 12, wherein the phytopathogenic microorganisms are fungal organisms.

* * * * *